US009999591B2

(12) United States Patent
Guerry et al.

(10) Patent No.: US 9,999,591 B2
(45) Date of Patent: *Jun. 19, 2018

(54) IMMUNOGENIC COMPOSITION AGAINST CAMPYLOBACTER JEJUNI

(71) Applicant: The United States of America as Represented by the Secretary of the Navy, Washington, DC (US)

(72) Inventors: Patricia Guerry, Silver Spring, MD (US); Mario Artur Monteiro, Guelph (CA)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/733,114

(22) Filed: Jun. 8, 2015

(65) Prior Publication Data

US 2015/0273037 A1 Oct. 1, 2015

Related U.S. Application Data

(63) Continuation-in-part of application No. 11/524,057, filed on Sep. 20, 2006, now Pat. No. 9,084,809.

(60) Provisional application No. 60/722,086, filed on Sep. 21, 2005, provisional application No. 62/034,436, filed on Aug. 7, 2014, provisional application No. 62/165,301, filed on May 22, 2015, provisional application No. 62/054,454, filed on Sep. 24, 2014.

(51) Int. Cl.
| | |
|---|---|
| *A61K 9/00* | (2006.01) |
| *A61K 47/64* | (2017.01) |
| *A61K 31/715* | (2006.01) |
| *A61K 39/02* | (2006.01) |
| *A61K 39/00* | (2006.01) |

(52) U.S. Cl.
CPC .......... *A61K 9/0019* (2013.01); *A61K 31/715* (2013.01); *A61K 39/105* (2013.01); *A61K 47/646* (2017.08); *A61K 47/6415* (2017.08); *A61K 2039/55505* (2013.01); *A61K 2039/6037* (2013.01)

(58) Field of Classification Search
None
See application file for complete search history.

(56) References Cited

U.S. PATENT DOCUMENTS

| 4,761,283 A | * | 8/1988 | Anderson | ............ | A61K 39/092 |
| | | | | | 424/194.1 |
| 5,153,312 A | * | 10/1992 | Porro | ................... | A61K 39/092 |
| | | | | | 424/194.1 |
| 2011/0300173 A1 | | 12/2011 | Guerry et al. | | |

FOREIGN PATENT DOCUMENTS

| WO | WO2005020964 A1 | 3/2005 |
| WO | WO2007038122 A2 | 4/2007 |
| WO | WO2009017666 A1 | 2/2009 |

OTHER PUBLICATIONS

Newman. Exp. Opin. Ther. Patents (2000) 10(3):279-314.*
McNally et al. The FEBS Journal, issue 17, 272:4407-4422, Sep. 2005 first published Aug. 15, 2005.*
Chen, Yu-Han. Doctoral Thesis: Campylobacter Jejuni Polysaccharides and Conjugate Vaccines Thereof, 2011.*
St. Michael et al. Eur. J. Biochem. 269:5119-5136, 2002.*
McNally et al. Canadian Journal of Chemistry. 84:676-684 (2006).*
Maue, A et al. A Capsule Conjugate Vaccine Approach to Prevent Diarrheal Disease Caused by Campylobacter Jejuni. Human Vaccines & Immunotherapeutics. Jun. 2014, col. 10, No. 6, pp. 1499-1504. http://dx.doi.org/10.4161/hv.27985. Relevant to Claims 1-14.
Guerry, P et al. Campylobacter Polysaccharide Capsules: Virulence and Vaccines. Frontiers in Cellular and Infection Microbioogy. Feb. 15, 2012, vol. 2, Article 7, pp. 1-11. DOI: 10.3389/fcimb.2012.00007. Relevant to Claims 1-14.
Supplementary Partial European Search Report issued in EP Appln. No. 15830474.1 dated Dec. 14, 2017.
Poly, F. et al. Journal of Clinical Microbiology, vol. 49, No. 5, Mar. 16, 2011, pp. 1750-1757.
Holst-Sorensen, M. et al. Frontiers in Cellular Infection and Microbiology, vol. 2. Feb. 20, 2012, pp. 1-11.
Karlyshev, A. et al. Molecular Microbiology, vol. 55, No. 1, Jan. 1, 2005, pp. 90-103.
Papp-Szabo et al. Carbohydrate Research, vol. 340, No. 13, Sep. 26, 2005, pp. 2218-2221.

* cited by examiner

*Primary Examiner* — Oluwatosin A Ogunbiyi
(74) *Attorney, Agent, or Firm* — Diane P. Tso; Ning Yang; Albert M. Churilla

(57) ABSTRACT

The inventive subject matter relates to an immunogenic composition against *Campylobacter jejuni* comprising isolated capsule polysaccharide from selected pathogenic *Campylobacter jejuni* strains. The inventive subject matter also relates to methods of using the polysaccharide compositions in inducing and anti-*C. jejuni* immune response.

13 Claims, 22 Drawing Sheets

IMMUNOGENIC COMPOSITION AGAINST *CAMPYLOBACTER JEJUNI*

CROSS-REFERENCES TO RELATED APPLICATIONS

This application is a Continuation-in-Part to U.S. Nonprovisional application Ser. No. 11/524,057, now U.S. Pat. No. 9,084,809 B2, filed Sep. 20, 2006, which claims priority to U.S. Provisional application 60/722,086, filed Sep. 21, 2005, which are hereby incorporated by reference. This application also claims the benefit of U.S. Provisional application 62/054,454, filed Sep. 24, 2014; U.S. Provisional application 62/127,927, filed Mar. 4, 2015; U.S. Provisional application 62/034,436, filed Aug. 7, 2014; and U.S. Provisional application 62/165,301, filed May 22, 2015, which are hereby incorporated by reference.

BACKGROUND OF INVENTION

Field of the Invention

The inventive subject matter relates to an immunogenic composition capable of conferring protection against diarrhea caused by *Campylobacter jejuni* and a method of inducing an immune response against *C. jejuni* using the immunogenic composition.

Description of Related Art

*Campylobacter jejuni* is estimated to cause 2.5 million cases annually in the United States and >400 million cases worldwide. In developing countries *C. jejuni* is, like ETEC, primarily a pediatric disease. The symptoms of *campylobacter* enteritis include diarrhea, abdominal pain, fever and sometimes vomiting. Stools usually contain mucus, fecal leukocytes and blood, although watery diarrhea is also observed. The disease is zoonotic, and wild and domesticated birds represent a major reservoir. *C. jejuni* is a major foodborne infection, most often being associated with contaminated poultry, but major outbreaks have been associated with water or raw milk contamination (44). *C. jejuni* is also associated with Reiter's syndrome and inflammatory bowel syndrome, but the major complication of *C. jejuni* enteritis is Guillain-Barré Syndrome (GBS), a post-infectious polyneuropathy that can result in paralysis (Allos, B. M., J. Infect. Dis 176 (Suppl 2):S125-128 (1997)). The association is due to molecular mimicry between the sialic acid containing-outer core of the lipooligosaccharide (LOS) and human gangliosides (Moran, et al., J. Endotox. Res. 3: 521 (1996)). Thus, antibodies generated against LOS cores result in an autoimmune response to human neural tissue.

*C. jejuni* capsular moieties are important in serodetermination. However, despite over 47 Penner serotypes of *C. jejuni* having been identified, most *Campylobacter* diarrheal disease is caused by *C. jejuni* expressing only a limited number of serotypes. Therefore, only selected strains of *C. jejuni*, predicated on epidemiological studies, provides suitable candidate strains for development of vaccine compositions. However, despite the importance of this organism to human disease, there are no licensed vaccines against *C. jejuni*.

LOS synthesis in *Campylobacter* is controlled by a number of genes, including genes encoding enzymes involved in biosynthesis of sialic acid for incorporation into LOS. Thus, *C. jejuni* is one of a limited number of bacteria that can endogenously synthesize sialic acid, a 9 carbon sugar that is found in many mammalian cells. This is consistent with the observed molecular mimicry of LOS and human gangliosides important in GBS (Aspinall, et al., Eur. J. Biochem., 213: 1029 (1993); Aspinall, et al., Infect. Immun. 62: 2122-2125 (1994); Aspinall, et al., Biochem., 33: 241 (1994); Salloway et al., Infect. Immun., 64: 2945 (1996)).

An interesting recent revelation regarding the *Campylobacter* genome sequence was the presence of a complete set of capsule transport genes similar to those seen in type II/III capsule loci in the Enterobactericeae (Parkhill et al., Nature, 403: 665 (2000); Karlyshev et al., Mol. Microbiol., 35: 529 (2000)). Subsequent genetic studies in which site-specific mutations were made in several capsule transport genes indicated that the capsule was the serodeterminant of the Penner serotyping scheme (Karlyshev et al., Mol. Microbiol., 35: 529 (2000)). The Penner scheme (or HS for heat stable) is one of two major serotyping schemes of campylobacters and was originally thought to be based on lipopolysaccharide O side chains (Moran and Penner, J. Appl. Microbiol., 86: 361 (1999)). Currently it is believed that the structures previously described as O side chains are, in fact, capsules.

SUMMARY OF THE INVENTION

The inventive composition relates to an immunogenic composition comprising polysaccharide antigens comprising isolated capsule polysaccharides from a *Campylobacter jejuni* strain, linked to form polysaccharide polymers. The polysaccharides are isolated from lipooligosaccharide structures and other structures associated with Guillain Barré Syndrome or autoimmune disorders. The embodied composition comprises one or more polysaccharide antigens each comprising isolated polysaccharides from the *C. jejuni* strains selected from the group consisting of HS1, HS1/HS44, HS44, HS2, HS3, HS4, HS5, HS13, HS4/13/64, and HS50.

Another embodiment is a method of inducing an immune response by administering an immunogenic composition comprising one or more polysaccharide antigens with each antigen comprising an isolated polysaccharides or polysaccharide polymer derived from a *C. jejuni* strain where the *C. jejuni* strains are selected from the group consisting of: HS1, HS1/HS44, HS44, HS, HS3, HS4, HS5, HS13, HS4/13/64, and HS50. The composition is devoid of lipooligosaccharide structures and other structures associated with Guillain Barré Syndrome or other autoimmune disorders.

Another embodiment is a method of immunizing against *C. jejuni* strains HS4, HS13, HS4/13/64 and HS50 by administering one or more antigens, wherein each antigen comprises an isolated polysaccharide or polysaccharide polymers derived from a *C. jejuni* strain selected from the group consisting of HS4, HS13, HS4/13/64 and HS50.

Another embodiment is a method of immunizing against *C. jejuni* strains HS1, HS1/HS44, HS44 by administering one or more antigens, wherein each antigen comprises an isolated polysaccharide or polysaccharide polymer derived from a *C. jejuni* strain selected from the group consisting of *C. jejuni* strains HS4, HS13, HS4/13/64.

DETAILED DESCRIPTION OF PREFERRED EMBODIMENTS

The term "polysaccharide antigen" as used herein refers to a capsule polysaccharide derived from *Campylobacter jejuni* (*C. jejuni* or *Campylobacter jejuni*) capsule. As used, herein, each polysaccharide antigen comprises a polysaccharide or polysaccharide polymer derived from one *C. jejuni* strain. The inventive composition can be comprised of multiple polysaccharide antigens. As used herein, "polysaccharide" refers to two or more monosaccharide units composing a carbohydrate polymer molecule. A "polysaccharide polymer" refers to two or more polysaccharide molecules connected together. As used herein, "n" in the polysaccharide structure refers to the number of polysaccharide repeats in the polymer and is 1 or more and can be up to 100.

An embodiment of the current invention comprises polysaccharide antigens comprising a polysaccharide or polysaccharide polymer derived from the capsule of a *C. jejuni* strain. The strains from which the capsule polysaccharides are isolated are selected from the group consisting of HS1, HS1/HS44, HS44, HS2, HS3, HS4, HS5, HS13, HS4/13/64, and HS50. A capsule polysaccharide polymer comprises 1 to 100 copies of a polysaccharide structure, derived from an individual *C. jejuni* strain, connected together to form a polysaccharide polymer. The inventive immunogenic composition one or more polysaccharide antigens with each polysaccharide antigen comprising an isolated *C. jejuni* polysaccharide structure or polysaccharide polymer from a *C. jejuni* strain. The polysaccharides are isolated or purified away from lipooligosaccharide, or other structures associated with GBS or other autoimmune disorders.

A large number of the *C. jejuni* strains are identified. An embodiment of the current invention includes only capsule polysaccharides derived from *C. jejuni* strains, which have been shown to result in disease in humans.

Example 1: HS1/HS44 and HS44 Polysaccharide Structure

Vaccine strategies against *C. jejuni* have been largely limited due to the molecular mimicry between lipooligosaccharide (LOS) cores of many strains of *C. jejuni* and human gangliosides (Moran, et al., J. Endotox. Res., 3: 521 (1996). This mimicry is thought to be a major factor in the strong association of *C. jejuni* infection with Guillain Barre Syndrome (GBS), a post-infectious polyneuropathy (Allos, J. Infect. Dis., 176(Suppl.): S125-128 (1997)). Thus, antibodies generated against LOS cores result in an autoimmune response to human neural tissue. It has been estimated that as many as 1/3000 cases of *campylobacter* enteritis results in GBS. Therefore, the possibility of developing GBS could be associated with any whole cell vaccine against *C. jejuni* that includes ganglioside mimicry.

Figure 1:
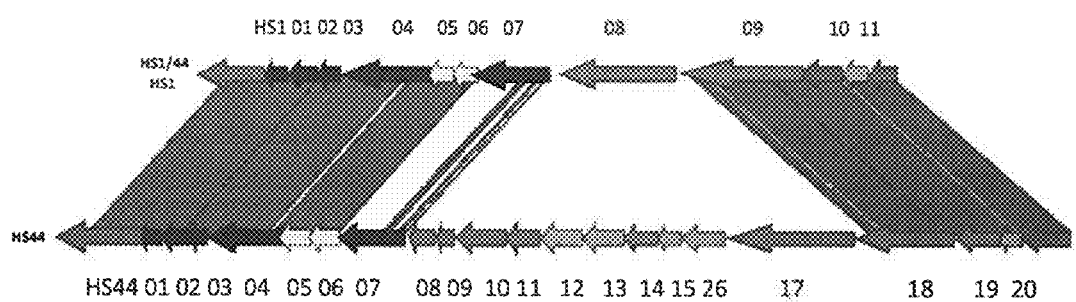
FIG. 1. Alignment of variable CPS loci from *C. jejuni* HS1 and HS44 Penner type strains. Genes are as indicated in the figure and include: methyl phosphoramidate (MeOPN) biosynthesis and transferase; CPS transport and assembly; putative methyl transferase; Heptose/deoxyheptose biosynthesis; putative glycosyl transferase; sugar biosynthesis; and hypothetical.

Recent development of a molecular CPS typing system re-enforced the strong correlation between CPS and Penner types (Poly, et al., J. Clin. Microbiol. 49: 1750 (2011)). Both Penner serotyping and molecular CPS typing have revealed the predominance of a handful of CPS types worldwide. Among CPS types, the HS1 complex is one of the most common, accounting for 8.2% of *C. jejuni* induced diarrhea worldwide ((Poly, et al., J. Clin. Microbiol. 49: 1750 (2011); Pike, et al., plOs One 8: e67375 (2013)). This complex is composed of HS1 and HS44 types, and strains can serotype as HS1, HS44 or HS1/44. So far, only the CPS structure of the HS1 type strain has been described, which is composed of repeating units composed of 4-substituted α-D-galactose (Gal) and glycerol (Gro) linked by phosphate (P) in a teichoic acid-like structure [-4)-α-D-Galp-(1-2)-Gro-(1-P-]$_n$ (Aspinall, et al., Eur. J. Biochem. 216: 880 (1993)). The HS1 CPS backbone may be decorated by β-D-fructofuranoses (Fru) branches, at C-2 and C-3 of the Gal unit, which in turn may be decorated at C-3 with MeOPN (FIG. 1; (McNally, et al., FEBS J. 272: 4407 (2005)). Both the fructofuranose branches and MeOPN are found in non-stoichiometric amounts, presumably due to phase variation at homopolymeric tracts of bases in the genes encoding their respective transferases (McNally, et al., FEBS J. 272: 4407 (2005)). The ~15 kb HS1 CPS locus encoding eleven genes for the synthesis of this polysaccharide (BX545859) is the smallest CPS locus identified to date in *C. jejuni* (Karlyshev, et al., Appl. Environ. Microbiol. 71: 4004 (2005)) (FIG. 1).

The HS1 type strain used was MSC57360 and the HS44 strain (ATCC 43463) was obtained from the American Type Culture Collection (ATCC)(Manassas, Va.). *C. jejuni* strain CG98-U-77 was isolated from a diarrhea case from Thailand and was obtained from the Armed Forces Research Institute of Medical Sciences (AFRIMS). *C. jejuni* strains were routinely cultured at 37° C. under microaerobic conditions (5% $O_2$, 10% $CO_2$, and 85% $N_2$) on Mueller Hinton (MH) agar plates, supplemented with the appropriate antibiotic, if required. *E. coli* strains were grown in LB media supplemented with the appropriate antibiotics.

*C. jejuni* genomic DNA was extracted from 16 hour cultures. Sequencing of the CPS loci was performed as previously described (Karlyshev, et al., Mol. Microbiol. 55: 90 (2005); Poly, et al. J. Clin. Microbiol. 49: 1750 (2011); Karlyshev, et al., Gene 522: 37 (2013)).

The CPS was extracted from cells by hot water-phenol extraction for 2 hours at 70° C. The aqueous layer was dialyzed (1000 Da) against water followed by ultracentrifugation to separate the CPS from the LOS. The supernatant material containing the CPS was subjected to size-exclusion chromatography (Sephadex G50) for further purification to yield the intact CPSs.

Determination of monosaccharide composition was performed using a procedure amenable to the alditol acetate method (Chen, et al., Carbohydr. Res. 343: 1034 (2008)) with the alditol acetates being analyzed in a ThermoFinnigan POLARIS™-Q (Thermo Fisher Scientific, Inc, Waltham, Mass.) gas chromatograph/mass spectrometer (GC/MS) using a DB-17 capillary column. The sugar linkage types were characterized by characterization of the permethylated alditol acetates by GC/MS as previously described (Chen, et al., Carbohydr. Res. 343: 1034 (2008)). The NMR experiments were performed on a Bruker 400 MHz spectrometer (Bruker Corporation, Billeria, Mass.) equipped with a Broker cryo platform at 295 K with deuterated trimethylsilyl propanoic acid and orthophosphoric acid as external standards.

The variable region containing the genes for synthesis of the polysaccharide are located between the conserved genes encoding the ABC transporter involved in capsule synthesis and assembly (FIG. 1), which also shows the variable region of the HS1 CPS locus (McNally, et al., FEBS J. 272: 4407 (2005)). The DNA sequence of the capsule locus of the HS44 type strain contained homologs of 10 of the 11 genes found in HS1, missing only HS1.08, a gene of unknown function (FIG. 1). The gene content of HS44 capsule biosynthesis locus is summarized in Table 1. All shared homologs were >96% identical, except for the putative MeOPN transferase (HS44.07) which showed only 47% identity to that of HS1.

TABLE 1

| Locus Tag | Putative function[a] | Relationship | Identity with HS1[b] | Size (amino acid) |
|---|---|---|---|---|
| HS44.01 | MeOPN biosynthesis | HS1.01 | 184/170 (96%) | 170 |
| HS44.02 | MeOPN biosynthesis | HS1.02 | 252/253 (99%) | 253 |
| HS44.03 | MeOPN biosynthesis | HS1.03 | 197/200 (98%) | 200 |
| HS44.04 | MeOPN biosynthesis | HS1.04 | 775/779 (99%) | 779 |
| HS44.05 | Methyl transferase | HS1.05 | 253/253 (100%) | 253 |
| HS44.06 | Methyl transferase | HS1.06 | 255/257 (99%) | 257 |
| HS44.07 | MeOPN transferase | HS1.07 | 308/642 (47%) | 809 |
| HS44.08 | sugar-phosphate nucleotidyltransferase | — | — | 224 |
| HS44.09 | sedoheptulose 7-phosphate isomerase | — | — | 201 |
| HS44.10 | D-glycero-D-manno-heptose 7-phosphate kinase | — | — | 360 |
| HS44.11 | GDP-mannose 4,6-dehydratase | — | — | 343 |
| HS44.12 | GDP-fucose synthetase (fcl) | — | — | 381 |
| HS44.13 | GDP-fucose synthetase (fcl) | — | — | 385 |
| HS44.14 | Cj1429 like | — | — | 310 |
| HS44.15 | Nucleotide-sugar epimerase/dehydratase | — | — | 181 |
| HS44.16 | Nucleotidyl-sugar pyranose mutase | — | — | 418 |
| HS44.17 | Heptosyl transferase | — | — | 1202 |
| HS44.18 | CDP glycerol glycerophosphotransferase | HS1.09 | 1087/1095 (97%) | 1100 |
| HS44.19 | Unknown | HS1.10 | 390/398 (98%) | 397 |
| HS44.20 | Glycerol-3-phosphate cytidylyltransferase | HS1.11 | 128/129 (99%) | 129 |

[a]Function attributed based on Blastp performed on non-redundant protein sequences database,
[b]Numbers in parenthesis are the percentage of identity between the HS1 and HS44 proteins.

The HS44 locus included an insertion of 10 additional genes between HS1.07 and HS1.09 encompassing 9,258 bp (Table 1, FIG. 1). These include 4 genes encoding enzymes predicted to be involved in deoxyheptose biosynthesis (HS44.08 to HS44.11) and three genes (HS44.12, HS44.13 and HS44.15) encoding proteins that are homologous to epimerase reductases that have been recently demonstrated to be involved in 6-deoxy-altro-heptose biosynthesis. The CPS locus of HS44 also includes a gene (HS44.14) similar to CJ1429c coding for a protein of unknown function in NCTC 11168 (HS2), a nucleotidyl-sugar pyranose mutase (HS44.16) and a putative heptosyltansferase (HS44.17, Table 1 and FIG. 1). In contrast, the DNA sequence of the variable CPS locus of a clinical isolate that typed as HS1/44 was identical with that of the type strain of HS1. The minimum protein homology predicted from the 11 genes in these two capsule loci was >99%.

Figure 2:
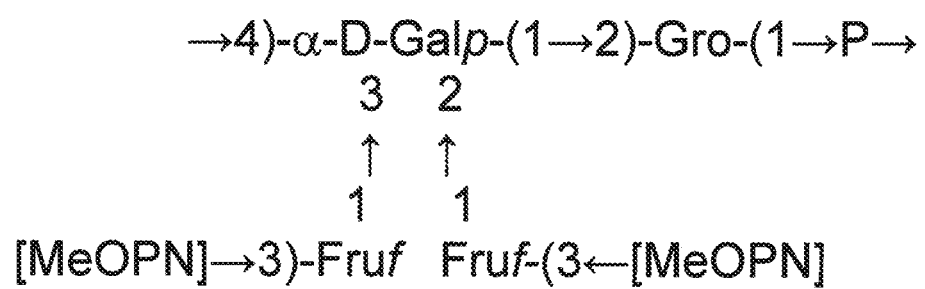
FIG. 2. Structure of HS1 teichoic acid-like capsule.

Fine structural analysis revealed that the polysaccharide structure of HS1/44 is similar to that of the previously described teichoic acid capsule polysaccharide (CPS) of HS1 strain (Aspinall, McDonald et al. 1993, McNally, Jarrell et al. 2005): →4)-[MeOPN→3)-β-D-Fru-(1→]-α-Gal-(1→2)-Gro-(1→P→ (FIG. 2).

Figure 3:
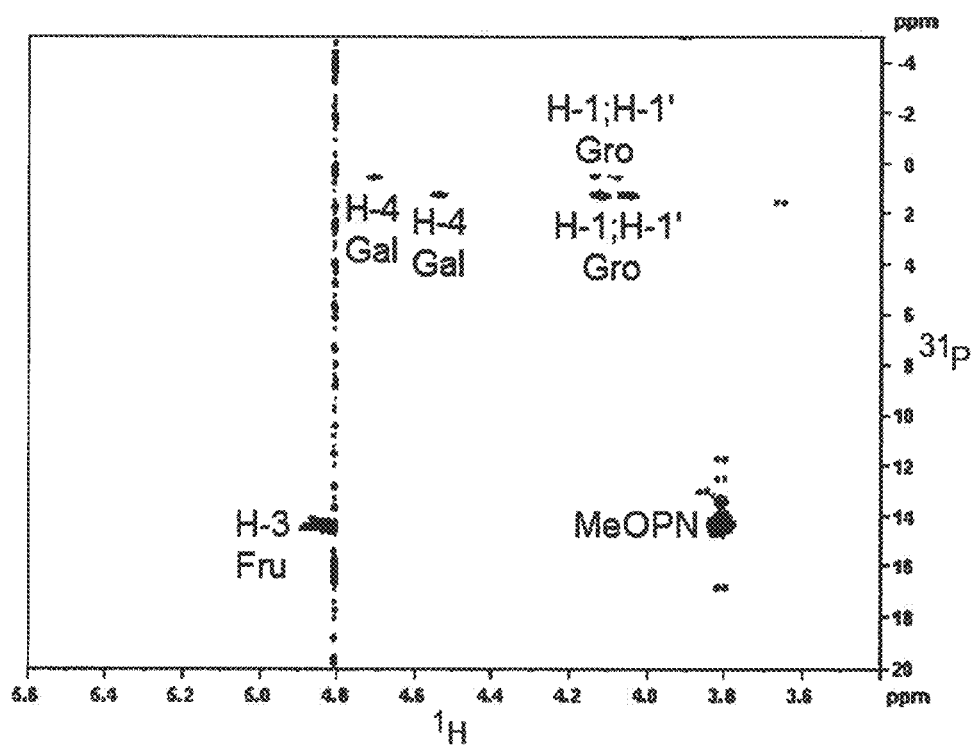
FIG. 3. 2D $^1$H-$^{31}$P HMBC NMR spectrum of *C. jejuni* HS:1/44 teichoic acid CPS. This NMR spectrum shows the connections between the MeOPN moieties and positions 3 of the Fru units, and between the diester-phosphate and position 4 of Gal and position 1 of Gro.

FIG. 3 shows the phosphorous-proton connections detected in HS1/44 CPS that emanate from the linkages of the teichoic-acid diester-phosphate ($\delta_P$ 0.5 and 1.5) to position 1 of Gro and position 4 of Gal, and from the attachment of the MeOPN ($\delta_P$ 14.3) to position 3 ($\delta_H$ 4.83) of Fru residues. The H-4 resonance of the 4-linked Gal carrying the Fru branches appeared at δ 4.68, whereas that of the defructosylated 4-linked Gal resonated at δ 4.49 (FIG. 3). A similar pattern was observed for the H-1 resonances of Gro. Simultaneous analysis of the HS1 type strain and HS1/44 CPSs, suggested that the HS1/44 CPS contained a lower degree of fructosylation, as judged by the lower intensities of the 2,3,4-trisubstituted Gal linkage (GC-MS) and MeOPN resonance ($^{31}$P NMR).

Figure 4:
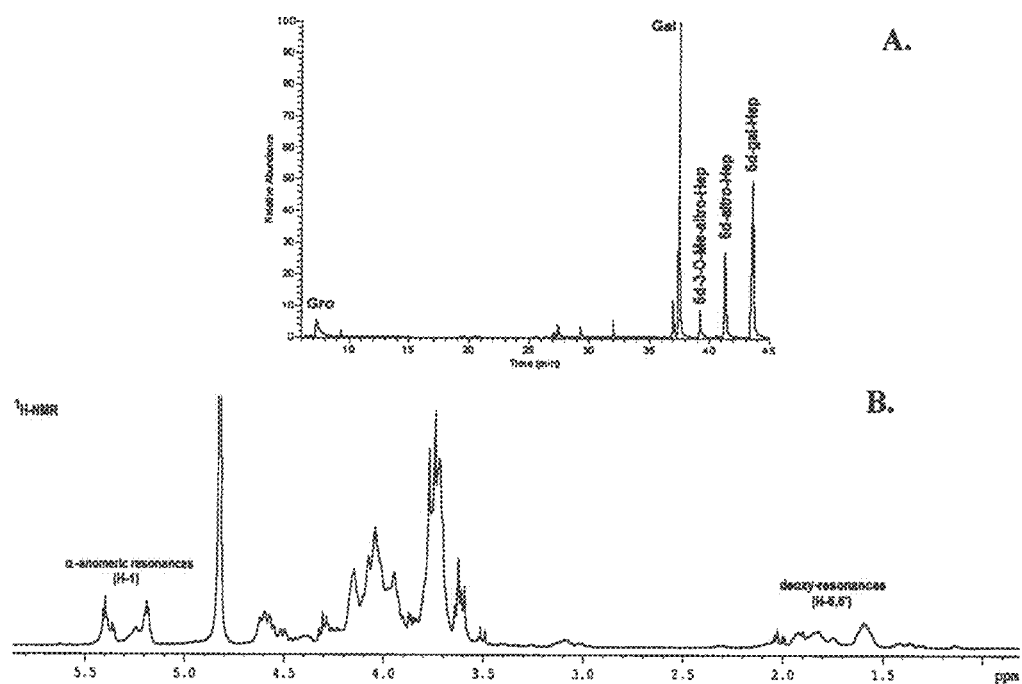
FIG. 4. GC-MS and NMR of *C. jejuni* HS44 CPS material. (A) GC-MS profile of the alditol acetate derivatives from the two CPSs of *C. jejuni* HS44, showing (i) the backbone units of the teichoic acid CPS, glycerol (Gro) and galactose (Gal), and (ii) those emanating from the second heptose-rich CPS, 6-deoxy-3-O-Methyl-altro-heptose (6d-3-O-Me-altro-Hep), 6-deoxy-altro-heptose (6d-altro-Hep) and 6-deoxy-galacto-heptose (6d-gal-Hep). (B)$^1$H NMR spectrum of HS44 CPS material showing the α-anomeric resonances emanating from 6d-altro-Hepf, 6-deoxy-galacto-Hepf and 6d-3-O-Me-altro-Hepf of the heptose-rich CPS and from Gal of the teichoic acid CPS.

Analysis of HS44 CPS material identified two distinct polysaccharide capsule structures. One CPS was analogous to the aforementioned teichoic-acid CPS of HS1 and HS1/44 (FIG. 2), but in which no MeOPN-containing Fru branches were observed. The second CPS was rich in heptoses, being composed of repeating blocks of 6-deoxy-galacto-heptose (6d-gal-Hep), 6-deoxy-altro-heptose (6d-altro-Hep) and, in lesser amounts, 6-deoxy-3-O-methyl-altro-heptose (6d-altro-3-O-Me-Hepf). The heptose configurations were characterized by comparison with well-defined synthetic standards by GC. The linkage-type analysis (GC-MS) (FIG. 4A) revealed that the deoxy-heptoses were present in part as terminal and 2-substituted units in the furanose form.

Accompanying NMR studies (FIG. 4B) confirmed the presence of deoxy-heptoses ($\delta_H$ 1.5-2.0) and revealed that these units were present in the α anomeric configuration ($\delta_P$ 5.15-5.42). A new MeOPN moiety Op 14.0), different from that expressed by HS1 and HS1/44 was associated with HS44 CPS material. This is consistent with the divergence of the putative MeOPN transferase observed in this strain.

The product of the HS1.08 gene encodes a predicted protein of 849 amino acids, annotated as a putative sugar transferase (Karlysheev, et al., Mol. Microbiol. 55: 90 (2005)). Because the HS44 teichoic acid-like CPS lacked the non-stoichiometric fructose branch and the HS1.08 gene was missing from the capsule locus, we hypothesized that HS1.08 encoded a fructose transferase. A mutant in this gene expressed a lower MW capsule as on an Alcian blue stained gel and the MW was restored to that of wildtype in the complement as shown by gel; NMR analysis also confirmed complementation, but the lower intensity of the MeOPN resonance in the $^{31}$P NMR (FIG. 5B) suggested that complementation in this case was partial. Thus, HS1.08 appears to encode a transferase that can transfer Fru to Gal.

Figure 5:
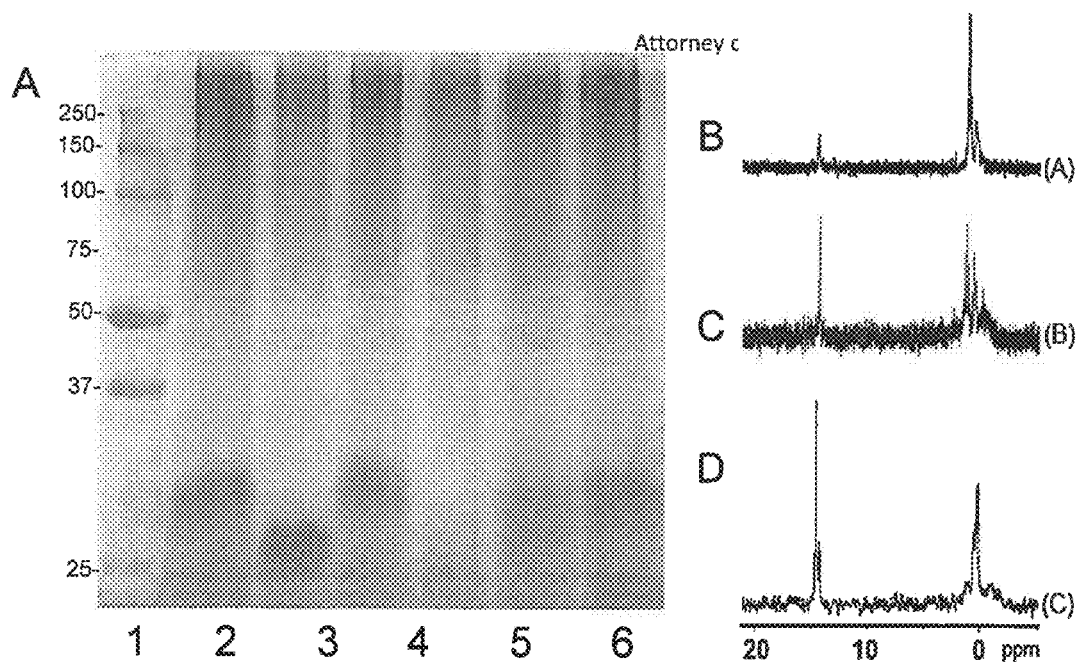
FIG. 5. Characterization of mutants in the HS1 CPS locus. A. Alcian blue stained 12.5% SDS PAGE of crude CPS preparations. Lane 1, Precision Plus protein standards; lane 2, HS1 wildtype; lane 3, HS1 1.08 mutant; lane 4, HS1 1.08 mutant complemented; lane 5, HS1 1.09 mutant; lane 6, HS1 1.09 mutant complemented; lane 7, HS1 wildtype. B. $^{31}$P NMR of CPS from HS1.08 complement; C. $^{31}$P NMR of CPS from HS1.09 complement; D. $^{31}$P NMR of CPS from HS1 wildtype.

Gene HS1.09 was annotated as a putative CDP glycerol transferase (Karlyshev et al., 2005). Mutation of this gene in HS1 resulted in the loss of CPS as detected by Alcian blue staining of an SDS-PAGE gel (FIG. 5A). Gel analysis of the complement of the mutant showed a faint CPS band (FIG. 5A), but restoration of CPS expression was confirmed by the $^{31}$P NMR spectrum which indicated the presence of MeOPN (FIG. 5B).

In one embodiment an immunogenic composition, useful for inclusion in a vaccine composition against HS1, HS1/HS44 and HS44 *C. jejuni* strains, comprises polysaccharide antigen, comprising the structure:

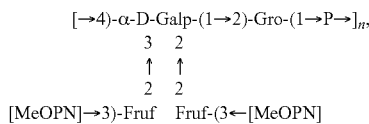

or a polymer comprising a repeating of the polysaccharide structure, wherein "n" is 1 to 100. The polysaccharide structure of HS44 comprises the above structure without "[MeOPN]→3)-Fruf" unit connected at the 2 or 3 position of Gal. Therefore, in another embodiment, an immunogenic composition would comprise a polysaccharide antigen with a repeating polysaccharide structure, derived from HS44 that comprises the structure:

[→4)-a-D-Galp-(1→2)-Gro-(1→P→]$_n$, wherein "n" is 1 to 100.

*Campylobacter Jejuni* Strain PG 3588 (HS:1):

Upon treatment of *Campylobacter jejuni* strain PG 3588 (HS:1) capsule polysaccharide (CPS) with mild acetic acid (5%), the fructose (Fruf) side branches and their accompanying MeOPN units were removed. The $^1$H NMR of the defructosylated CPS showed the anomeric resonance at δ 5.21 that corresponds to the α-D-Gal residue (without the Fruf substitutions). H5 δ 4.18 was assigned from the H6 δ 3.75 proton resonance, Gro resonances were found to be at H1/1'δ 4.05/4.12, H2 δ 3.98, and H3/3' 3.78/30.82.

All carbon resonances of *Campylobacter jejuni* strain PG 3588 (HS:1) capsule polysaccharide were assigned using a 2D $^1$H-$^{13}$C HSQC are summarized in Table 2. A 2D $^1$H-$^{31}$P HMBC (FIG. 4) showed a strong cross peak at ($\delta_H$ 4.54/$\delta_P$ 1.14), and ($\delta_H$ 4.05, 4.11/$\delta_P$ 4.14) which confirmed the presence of the phosphodiester and its attachment to the Gro and to the C4 of Gal through a phosphodiester. Another resonance was detected in the 2D $^1$H-$^{31}$P HMBC at δ 14.04 for a MeOPN moiety, and it showed a cross peak at $\delta_H$ 3.75/$\delta_P$ 14.04, identifying the attachment of MeOPN at the C-6 of Gal.

TABLE 2

$^1$H, $^{13}$C chemical shifts of *C. jejuni* CPS PG 3588

| Sugar residue | H1/1' C1 | H2 C2 | H3/3' C3 | H4 C4 | H5 C5 | H6/6' C6 |
|---|---|---|---|---|---|---|
| α-D-Gal | 5.21 | 3.88 | 3.90 | 4.54 | 4.18 | 3.75 |
| | 100.84 | 71.05 | 71.10 | 77.31 | 73.45 | 63.42 |
| Gro | 4.05/4.12 | 3.98 | 3.78/3.82 | | | |
| | 67.23 | 79.81 | 63.95 | | | |

TABLE 2-continued

$^1$H, $^{13}$C chemical shifts of *C. jejuni* CPS PG 3588

| Sugar residue | H1/1'  C1 | H2  C2 | H3/3'  C3 | H4  C4 | H5  C5 | H6/6'  C6 |
|---|---|---|---|---|---|---|

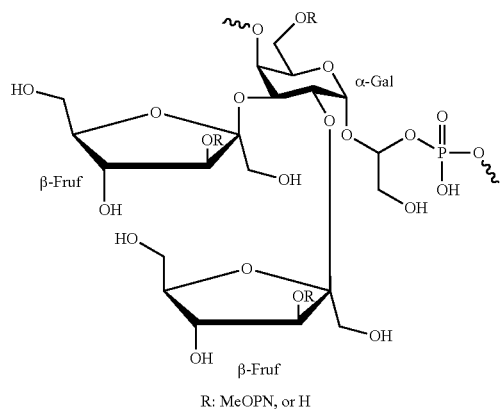

R: MeOPN, or H

Example 2: HS5 Derived Polysaccharide Structure

One embodiment is an immunogenic composition against *C. jejuni* that contains an isolated capsule polysaccharide structure or polymers of the structure derived from HS5. The polysaccharide structure comprises four variants, with the structures as follows:

i

```
        [MeOPN]⁻ —
              ↓
          K   7
       α-Dideoxy-Hep
              ↓
          A   6              Y
   →7)α-DD-Hep(1→3)Glucitol(6→P→
              2              2
              ↑              ↑
              1              1
       α-Dideoxy-Hep   α-Dideoxy-Hep
          7   N          7   L
              ↑              ↑
        [MeOPN]⁻ —      [MeOPN]⁻ —
``` ii

```
          C                  X
   →7)α-DD-Hep(1→2)Glucitol(6→P→
              2
              ↑
              1
       α-Dideoxy-Hep
          7   N
              ↑
        [MeOPN]⁻ —
``` iii

```
        [MeOPN]⁻ —
              ↓
          K   7
       α-Dideoxy-Hep
              ↓
          A   6              X
   →7)α-DD-Hep(1→2)Glucitol(6→P→
              2
              ↑
              1
       α-Dideoxy-Hep
          7   N
              ↑
        [MeOPN]⁻ —
``` iv

```
          B                  Z
   →7)α-DD-Hep(1→3)Glucitol(6→P→
              2              2
              ↑              ↑
              1              1
       α-Dideoxy-Hep   α-Dideoxy-Hep
          7   N          7   L
              ↑              ↑
        [MeOPN]⁻ —      [MeOPN]⁻ —
```

Figure 6:
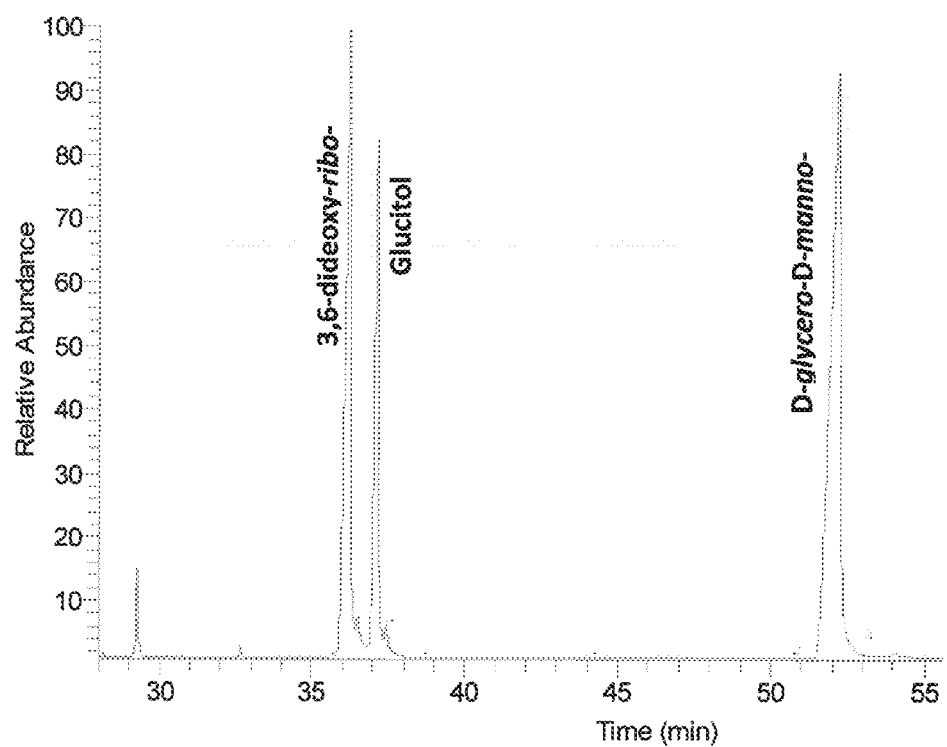
FIG. 6. The GC-MS profile of the alditol acetate derivatives of *C. jejuni* CG2995 CPS.

Results from monosaccharide composition analysis revealed that the capsule polysaccharide (CPS) of strain CG2995 (HS:5) contained 3,6-dideoxy-ribo-heptose, glucitol, and D-glycero-D-manno-heptose (FIG. 6). Multiple linkages of each residue were observed; terminal 3,6-dideoxy-ribo-heptose, 2,6-disubstituted Glucitol, 2,3,6-trisubstituted Glucitol, 2-monosubstituted D-glycero-D-manno-heptose, 2,6-disubstituted D-glycero-D-manno-heptose, 2,7-disubstituted D-glycero-D-manno-heptose, and 2,6,7-trisubstituted D-glycero-D-manno-heptose.

Figure 7:
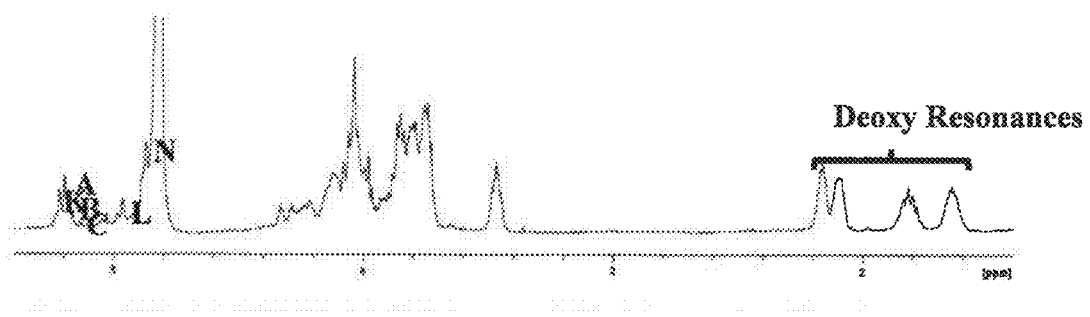
FIG. 7. The $^1$H NMR spectrum of *C. jejuni* CG2995 CPS.

The 1 D $^1$H NMR of the CPS revealed six anomeric peaks, three of which are associated with D-glycero-D-manno-heptose residues at 5.20 ppm, 5.18 ppm, and 5.16 ppm (A, B, C respectively), and 3 of which are associated with 3,6-dideoxy-ribo-heptose residues at 5.21 ppm, 4.96 ppm, and 4.87 ppm (K, L, N respectively) (FIG. 7). Linkages and ring resonances were then confirmed via 2D $^1$H-$^1$H COSY, TOCSY, and NOESY experiments. Linkages found through NMR experiments coincided with the linkages assigned by GC-MS.

Figure 8A:
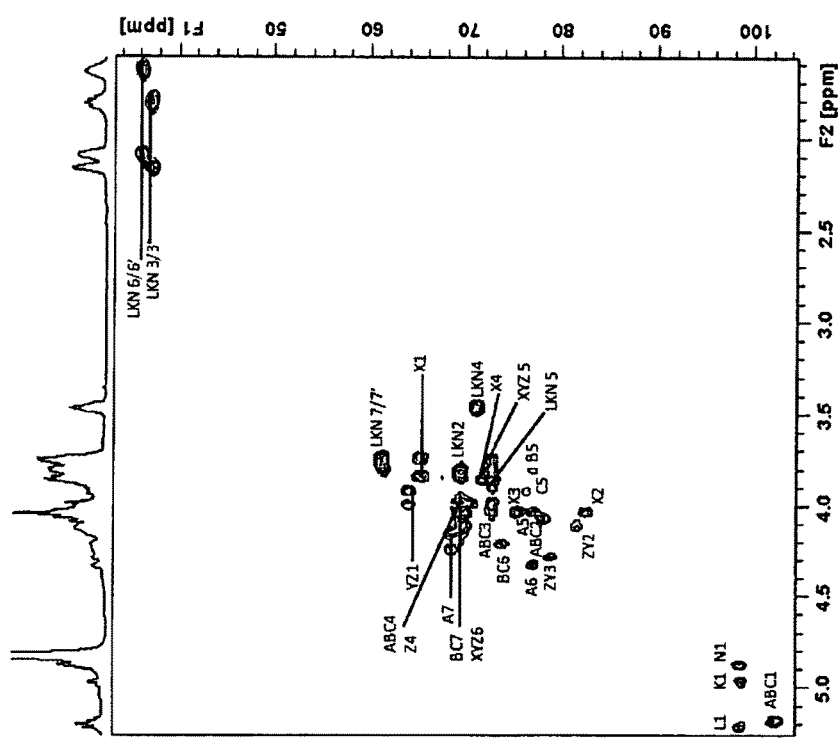
FIG. 8. (A) The 2D $^1$H-$^{13}$C HSQC NMR spectrum of *C. jejuni* CG2995 CPS; (B) The 1D selective $^1$H NOEs of the *C. jejuni* CG 2995 CPS. Irradiated peaks are denoted with an "*". Mixing time of 0.250 μs was used.
Figure 8B:
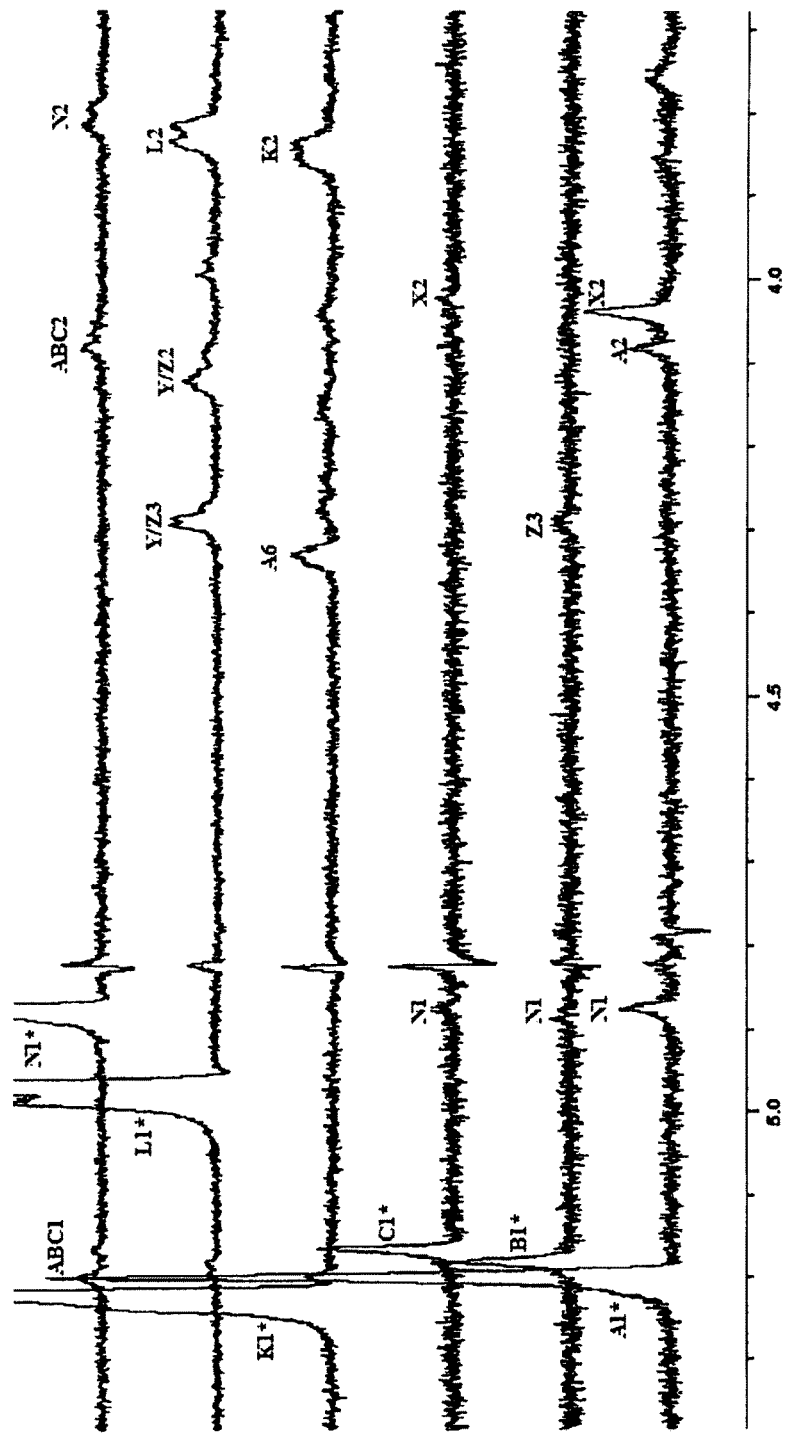

With the aid of 2D $^1$H-$^{13}$C HSQC and HMBC the Glucitol residues (X, Y, Z) could are assigned, along with the ring region resonances from the six heptose residues. As expected carbons involved in the glycosidic linkages, C2 (δ 78.1) of the D-glycero-D-manno-heptose A, B and C, C6 (δ 76.8) of D-glycero-D-manno-heptose A, C2 (δ 81.6) of Glucitol Y and Z, C2 (δ 82.5) of Glucitol X, and C3 (δ 78.8) of Glucitol Y and Z, were found to be down-field resonances (FIG. 8 (A)). The deoxy resonances associated with the 3,6-dideoxy-ribo-heptose were easily observed at δ 37.1 (C3) and δ 36.1 (C6). Selective 1D nOe experiments (FIG. 8(B)) also showed the presence of the linkages aforementioned.

Figure 9:
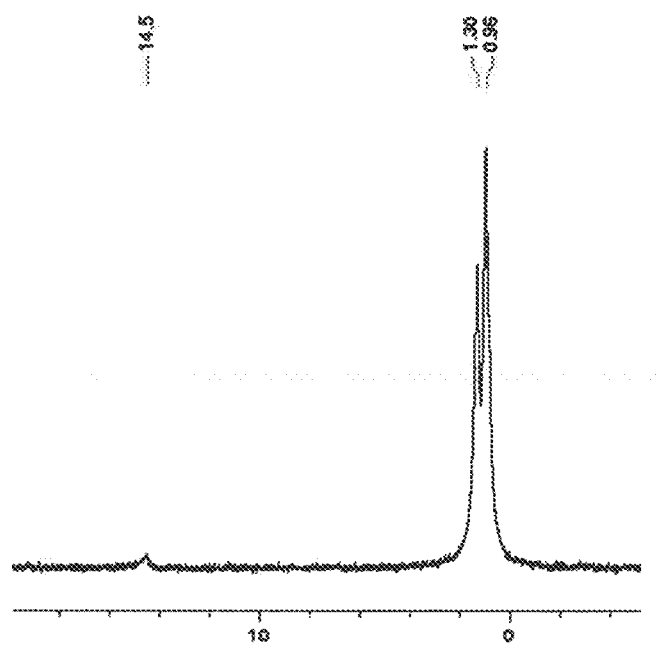
FIG. 9. The $^{31}$P NMR spectrum of *C. jejuni* CG2995 CPS.
Figure 10:
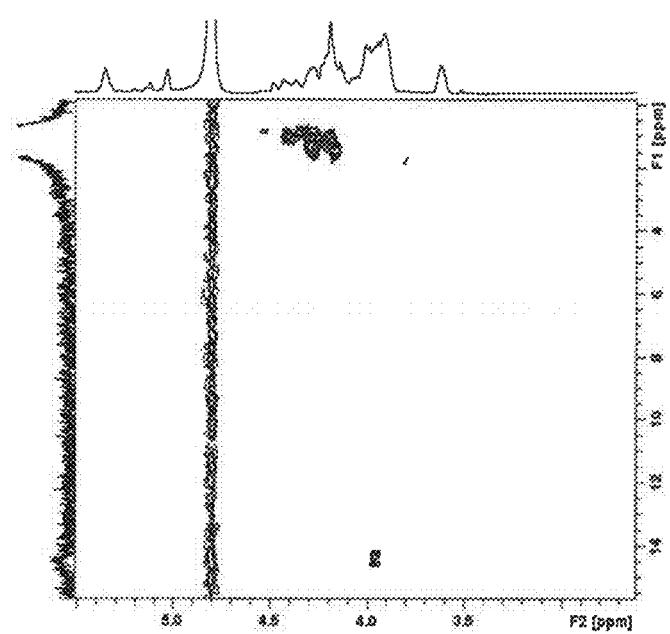
FIG. 10. The 2D $^1$H-$^{31}$P HMBC NMR spectrum of *C. jejuni* CG2995 CPS.

The 1D $^{31}$P and 2D $^1$H-$^{31}$P HMBC NMR revealed resonances at 0.96 and 1.30 ppm, indicating that the capsular polysaccharide repeats were linked with a phosphate bridge (FIG. 9). This bridge links through the 6-position of the Glucitol and the 7-position of the D-glycero-D-manno-heptose (FIG. 9). The 1D $^{31}$P spectra also gave rise to a peak δ 14.5 indicating MeOPN, and through the 2D $^1$H-$^{31}$P HMBC the MeOPN could be linked to being a 7-substituted 3,6-dideoxy-ribo-heptose (FIG. 10).

Figure 11:
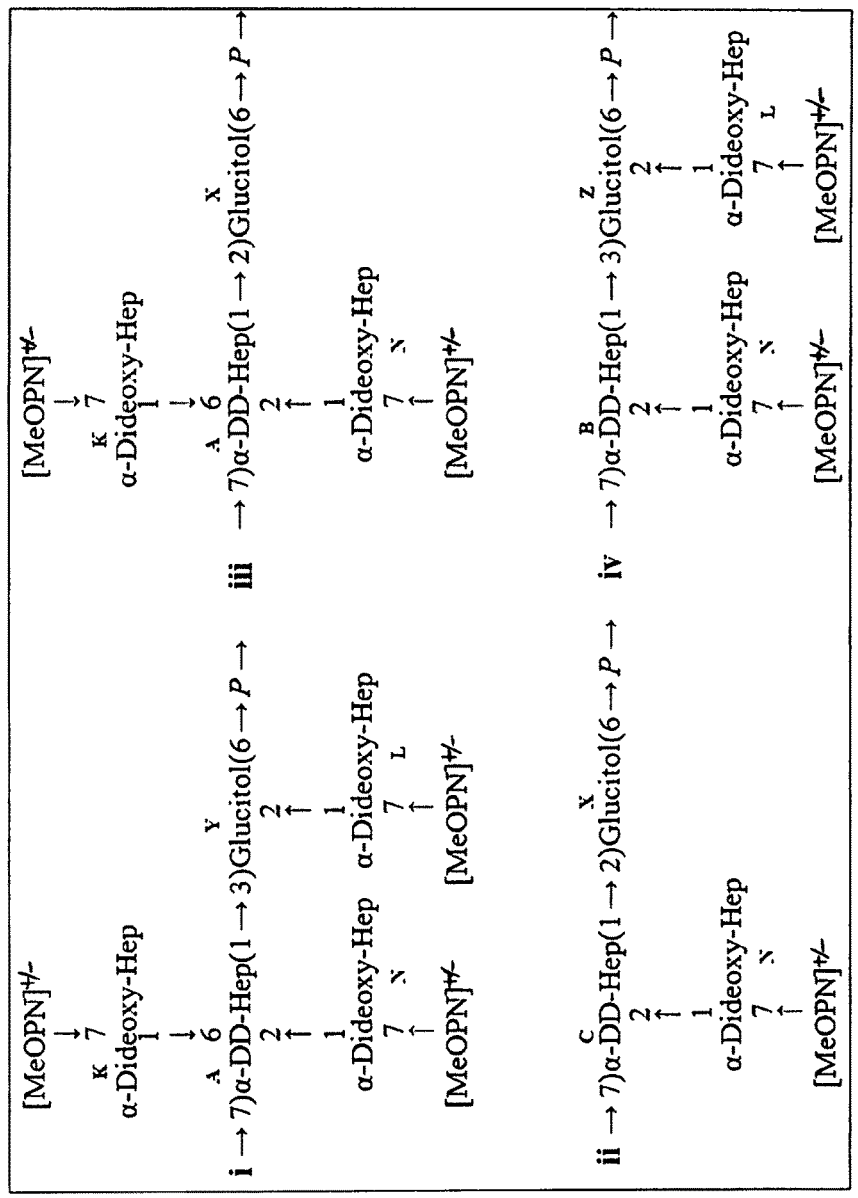
FIG. 11. Structure of HS5 CPS showing four variations: i) The main PS structure of *C. jejuni* CG2995, ii) variation 1, iii) variation 2, and iv) variation 3.

One main capsular polysaccharide was observed with a backbone of [-7)-α-D-glycero-D-manno-heptose-(1-3)-Glucitol-(6-)-P-] with 2,6-disubstitution of the D-glycero-D-manno-heptose, and 2-monosubstitution of the Glucitol with α-3,6-dideoxy-ribo-heptose (FIG. 11i). Three other variations of the capsular polysaccharide repeat were also noted; variation 1 with 2-monosubstituted D-glycero-D-manno-heptose and Glucitol linked through the 2-position instead of 3 to D-glycero-D-manno-heptose (FIG. 11ii), variation 2 with 2,6-disubstitution of the D-glycero-D-manno-heptose and Glucitol linked through the 2-position instead of 3 to D-glycero-D-manno-heptose (FIG. 11iii), and variation 3 with 2-monosubstituted D-glycero-D-manno-heptose and 2-monosubstituted glucitol (FIG. 11iv).

Example 3: Conjugation of CPS Polysaccharide to Protein Carrier

Figure 12:
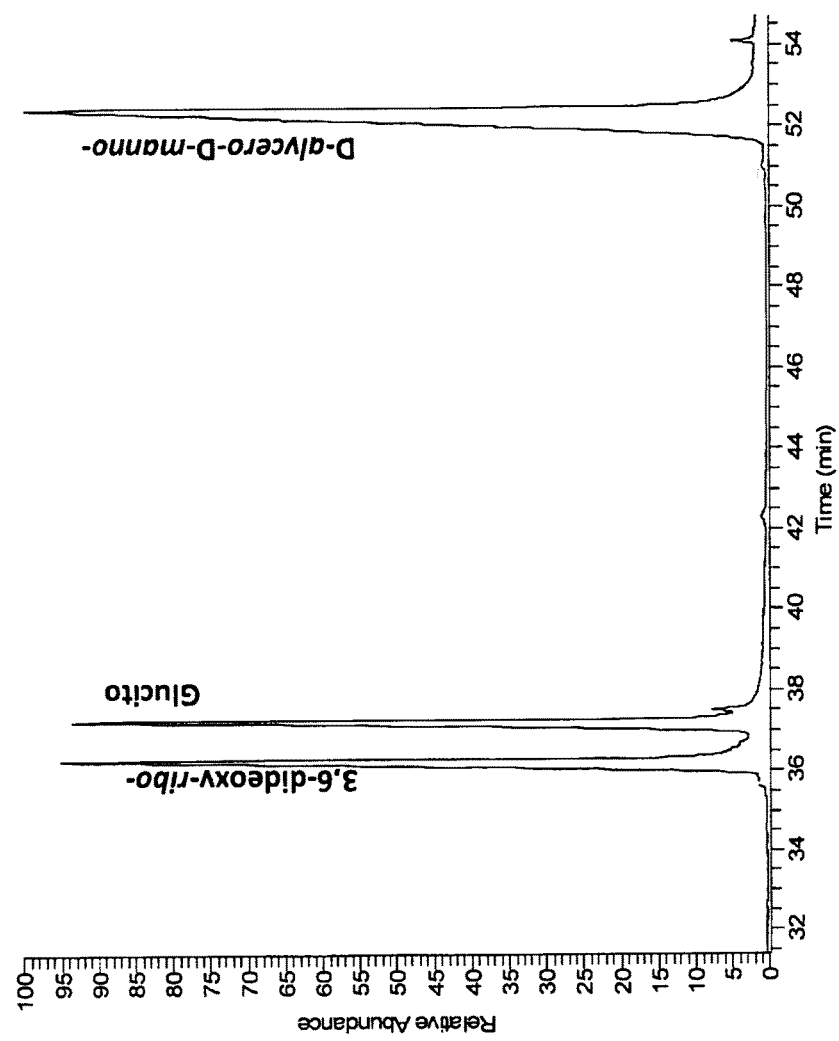
FIG. 12. The GC-MS profile (top) of the alditol acetate derivatives of *C. jejuni* CG2995 CPS, following TEMPO oxidation that shows a reduction in abundance of the 3,6-dideoxy-ribo-heptose.

One or more polysaccharides or polysaccharide polymers can be conjugated to a carrier molecule to improve immunity. The carrier, in one embodiment, is a protein carrier molecule. As an example protein carrier, $CRM_{197}$ can be conjugated to the polysaccharide or polysaccharide polymer. The GC-MS profile of the alditol acetate derivatives of C. jejuni CG2995 CPS, following TEMPO oxidation is shown in FIG. 12. Conjugation is illustrated in FIG. 13.

Conjugation of HS5 Polysaccharide

Isolated C. jejuni HS5 polysaccharide was conjugated to a protein structure and is described here as an illustration of conjugation of the polysaccharide or polysaccharide polymers. The overall scheme for conjugation is illustrated in FIG. 13. Any protein carrier is envisioned to be conjugated. Furthermore, conjugation to a protein carrier can be by any number of means.

Figure 13:
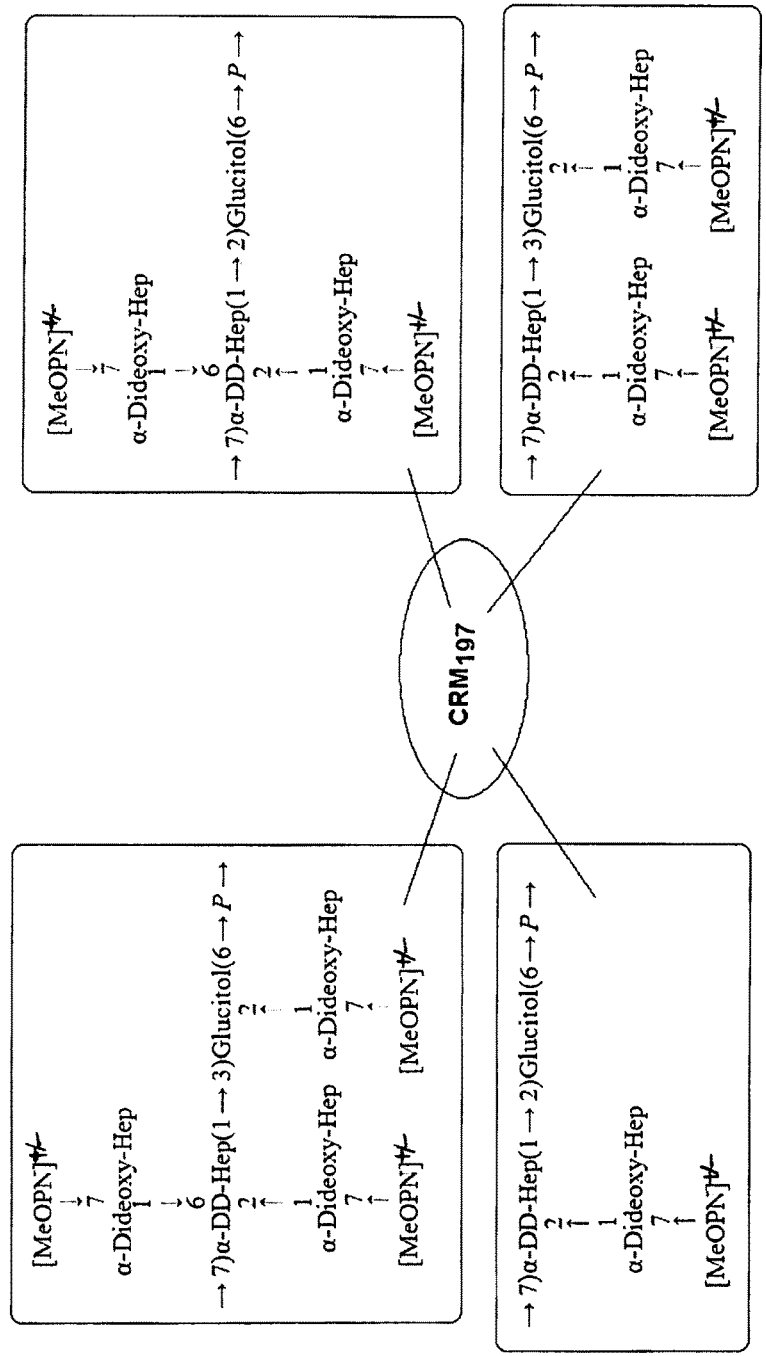
FIG. 13. TEMPO oxidation that shows a reduction in abundance of the 3,6-dideoxy-ribo-heptose, indicating that its C-7 primary hydroxyl (free of MeOPN) is the site of preferred oxidation in this CPS, and that which will be mostly involved in the conjugation of *C. jejuni* CG2995 CPS to carrier protein CRM197.

As an illustrative example, in FIG. 13 the polysaccharide was conjugated to $CRM_{197}$ by TEMPO-mediated oxidation. In this method, as shown in FIG. 13, the first step is oxidation of approximately 10% of the primary hydroxyls of the intact CPs to carboxylic acids via TEMPO-mediated oxidation. The scheme in FIG. 13 illustrates conjugation using the primary hydroxyl of the DD-Hep as one of the sites of oxidation. Non-stoichiometric oxidation may also occur at C-6 of Glc and at the $CH_2$—OH of the side-chain substituent. Following activation of the CPS, conjugation to the carrier protein (e.g., $CRM_{197}$) is accomplished, in the TEMPO-mediated method shown in FIG. 13, through carbodiimide coupling. Visualization of conjugation is by any means, such as gel electrophoresis.

Conjugation of HS1 Polysaccharide

Figure 14:
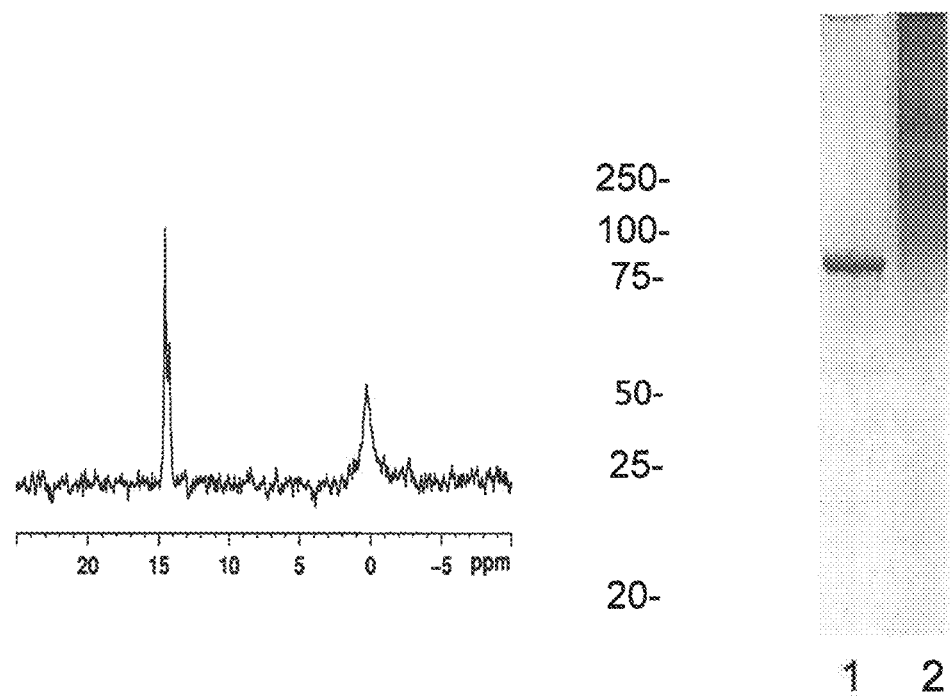
FIG. 14. Characterization of the HS1 conjugate vaccine. A. $^{31}$P NMR of HS1$_{CPS}$-CRM$_{197}$ conjugate vaccine showing the presence of MeOPN in the conjugate CPS. B. Gel code blue stained 12% SDS-PAGE gel. Lane 1, CRM$_{197}$; lane 2, HS1-CRM$_{197}$ conjugate. The mass of protein standards are shown on the left.

A glycoconjugate composed of HS1 teichoic acid CPS and the protein carrier $CRM_{197}$ was created through a conjugation scheme, similar to that used for HS5, based on stoichiometric oxidation of 10% of the available primary hydroxyls in the CPS. After oxidation of primary hydroxyls, the activated HS1 CPS was then conjugated to $CRM_{197}$ by carbodiimide-type coupling of the newly created carboxylic acid functionalities in the CPS and exposed $CRM_{197}$ lysine units. Importantly, analysis of the HS1 CPS-$CRM_{197}$ conjugate vaccine by NMR confirmed that the MeOPN and phosphate moieties remained intact during the conjugation manipulations. These results are shown in FIG. 14. A comparison of the intensities of the anomeric resonances in the partially oxidized HS1 CPS indicated that half of the backbone Gal residues were branched by the Fru-containing MeOPN units.

Example 4: Polysaccharides in HS Complexes

Polysaccharide structures were identified in C. jejuni Penner serotype complexes. For example, anti-HS4 serum results in cross-reaction to other strains of the HS4 complex, including HS13, HS4/13/64 and HS50 capsules. Isolation and analysis of the polysaccharides from these strains resulted in identification of disaccharides containing a common ido-heptose unit. The strains and isolated polysaccharide derived from the strains are listed in Table 3.

TABLE 3

HS4 complex capsule polysaccharide structures

| Serotype/Strain | Structure | |
|---|---|---|
| HS4 type strain | →3)-L-β-D-ido-Hep-(1→4)-β-D-GlcNAc-(1→ (non-stoichiometic MeOPN at C-4 of LD-ido-Hep) | |
| HS13 | →3)-6d-β-D-ido-Hep-(1→4)-β-D-Glc-(1→ (non stoichiometric MeOPN at C-2 and/or C-7 of 6d-ido-Hep); | (50%) and/or |
| | →3)-L-β-D-ido-Hep-(1→4)-β-D-Glc-(1→ | (50%) |
| HS4, 13, 64 (e.g., strain CG8486) | →3)-6d-β-D-ido-Hep-(1→4)-β-D-GlcNAc-(1→ (non stoichiometric MeOPN at C-2 and/or C-7 of 6d-ido-Hep); | (80%) and/or |
| | →3)-L-β-D-ido-Hep-(1→4)-β-D-GlcNAc-(1→ (non stoichiometric MeOPN at C-2 of LD-ido-Hep) | (20%) |
| HS50 | →3(-L-β-D-ido-Hep-(1→4)-β-D-Glc-(1→ (non stoichiometric MeOPN at C-4 of LD-ido-Hep); and/or | (85%) |
| | →3)-6d-β-D-ido-Hep-(1→4)-β-D-Glc-(1→ (non stoichiometric MeOPN at C-7 of 6d-ido-Hep) | (15%) |

Illustrated in Table 3, the common, surprising feature of these isolated capsule polysaccharides is the ido-heptose unit. As such, an embodiment is an immunogenic composition comprising one or more polysaccharide antigens, each comprising polysaccharide structures derived from these strains of C. jejuni.

The previously described CPS structure of C. jejuni strain CG8486 (HS: 4:13:64) consisted mainly of a disaccharide repeating unit [→3)-6d-β-D-ido-Hep-(1→4)-β-GlcNAc-(1→], with non-stoichiometric O-methyl phosphoramidate substituent attached to C-2 and C-7 positions of ido-heptose. A minor component of L-glycero-D-ido-heptose (LD-ido-Hep) was detected by GLC-MS, using alditol acetate derivatives for compositional analysis and permethylated alditol acetate derivates for linkage analysis of, and was newly found in this strain. The sugar ring configuration of 6-deoxy-heptose and L-glycero-D-heptose were assigned as idose. The traces of 1,7-anhydro-L-glycero-D-ido-heptose (1,7-anhydro-LD-ido-Hep) and 1,6-anhydro-L-glycero-D-ido-heptose (1,6-anhydro-LD-ido-Hep) originated from LD-ido-Hep during acid hydrolysis.

In addition to previously reported linkage types in C. jejuni CG8486 CPS (3-substituted 6d-ido-heptose [→3)-6d-ido-Hep-(1→] and 2,3-di-substituted 6d-ido-heptose [→2,3)-6d-ido-Hep-(1→], 3,7-di-substituted 6d-ido-heptose [→3,7)-6d-ido-Hep-(1→], 4-substituted N-acetyl-glucosamine [→4)-GlcNAc-(1→]), the GLC profile of GLC-MS of permethylated alditol acetate derivatives of C. jejuni HS:4:13:64 CPS showed two additional linkage types from LD-ido-Hep which were not detected in previously reported structure, including 3-substituted L-glycero-D-ido-heptose [→3)-LD-ido-Hep-(1→] and 2,3-di-substituted L-glycero-D-ido-heptose [→2,3)-LD-ido-Hep-(1→].

The 1D $^1H$ NMR of C. jejuni CG8486 CPS showed two resonances of two β-glycosides at δ 4.94 and δ 4.66 which were 6d-ido-Hep/LD-ido-Hep and GlcNAc, respectively. The presence of two anomeric proton resonances for three monosaccharide residues (6d-ido-Hep, LD-ido-Hep, and GlcNAc) suggested that both 6d-ido-Hep and LD-ido-Hep may contain the same chemical shifts through the sugar ring system except the H-6 position since the only difference between them was at the C-6 position with or without a hydroxyl group. The $^1$H NMR spectrum also revealed one methyl singlet at δ 2.07 which was characteristic of the N-acetyl moiety from GlcNAc and methylene signals at δ 1.77 and δ 2.03 which were 6-deoxy-moiety from 6d-ido-Hep. In addition, 1D $^{31}$P NMR detected a characteristic MeOPN signal at Sp 14.7. It was determined that the CPS of *C. jejuni* serotype HS4:13:64 (see Table 3) contained both 6-d-ido-Hep and LD-ido-Hep within its CPS:
- [→3)-6d-β-ido-Hep-(1→4)-β-GlcNAc-(1→] (with non-stoichiometric MeOPN at C-2 and/or C-7 of 6d-ido-Hep) as a major repeat; and
- [→3)-LD-β-ido-Hep-(1→4)-β-GlcNAc-(1→] (with non-stoichiometric MeOPN at C-2 of LD-ido-Hep) as a minor repeat.

CPS determination of *C. jejuni* HS:4 Type Strain (Strain MK7)

The CPS isolated from *C. jejuni* strain MK7 (HS4) was composed of L-glycero-D-ido-heptose (LD-ido-Hep) and N-acetyl-glucosamine (GlcNAc) by GC-MS profile determination of alditol acetate derivatives. The above CPS composition of *C. jejuni* HS:4 type strain was similar to previously reported CPS of serotype HS:4 complex (HS:4, 13,64; strain CG8486), which contains mostly 6-deoxy-ido-heptose (6d-ido-Hep) instead of LD-ido-Hep. GC-MS of permethylated alditol acetate derivatives showed the following linkage types of each monosaccharide: 3-substituted L-glycero-D-ido-heptose [→3)-LD-ido-Hep-(1→] and 4-substituted N-acetyl glucosamine [→4)-GlcNAc-(1→].

The $^1$H NMR spectrum of the *C. jejuni* strain MK7 (type strain HS:4) CPS showed two β-anomeric proton resonances at δ 4.70 and δ 4.94 for GlcNAc and LD-ido-Hep, respectively. The $^1$H NMR spectrum also revealed one methyl singlet at δ 2.07 which was characteristic of the N-acetyl moiety from GlcNAc and a broad range of overlapping sugar ring proton resonances between δ 3.50 and δ 4.55. In addition, 1D $^{31}$P NMR detected a weak trace of MeOPN signals at δp 14.3. The substituted sites of MeOPN could not be detected due to the small amount of MeOPN substitution in this HS:4 type strain.

CPS Determination of *C. jejuni* *C. Jejuni* Serotype HS:13 (Strain MK16)

*C. jejuni* HS4 type-strain (MK7) contains a CPS composed of the following disaccharide repeat: [→3)-L-β-D-ido-Hep-(1→4)-β-GlcNAc-(1→]. The monosaccharide composition analysis, using GC-MS of alditol acetate derivatives of *C. jejuni* strain MK16 (serotype HS:13) revealed the presence of glucose (Glc), 6-deoxy-ido-heptose (6d-ido-Hep), and L-glycero-D-ido-heptose (LD-ido-Hep) by GS-MS determination of alditol acetate derivative profiles. Linkage analysis of profiles of permethylated alditol acetate derivatives showed that these units were present as 4-substituted glucose [→4)-Glc-(1→], 3-substituted 6-deoxy-ido-heptose [→3)-6d-ido-Hep-(1→], 2,3-di-substituted 6-de-oxy-ido-heptose [→2,3)-6d-ido-Hep-(1→], 3-substituted L-glycero-D-ido-heptose [→3)-LD-ido-Hep-(1→], and 3,7-di-substituted 6-deoxy-ido-heptose [→3,7)-6d-ido-Hep-(1→]. In addition, a small amount of terminal glucose [Glc-(1→] was detected as the non-reducing end of the CPS. *C. jejuni* serotype HS:13 contains 4-substituted Glc as backbone instead of 4-substituted GlcNAc (seen in serotypes HS: 4:13:64 and HS:4).

Figure 15:
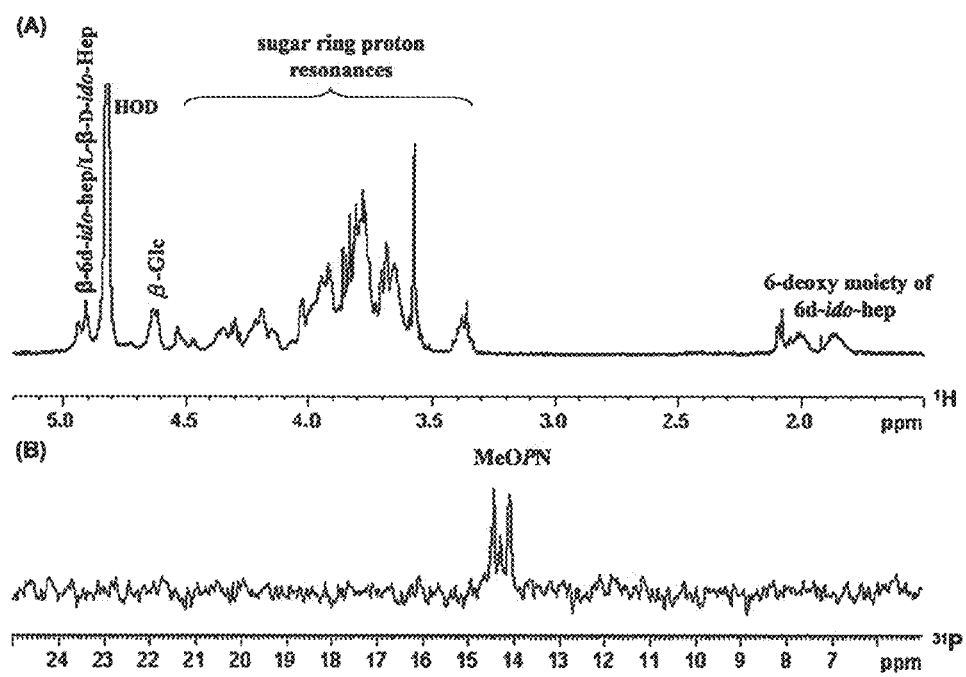
FIG. 15. NMR of HS:13 CPS. (A) 1D $^1$H NMR; and (B) 1D $^{31}$P NMR spectra of *C. jejuni* 3019 CPS (serotype HS:13).

The $^1$H NMR spectrum of *C. jejuni* serotype HS:13 CPS showed two β-anomeric proton resonances at δ 4.63 and δ 4.92 which assigned as Glc and 6d-ido-Hep/LD-ido-Hep, respectively (FIG. 15A). The $^1$H NMR spectrum also revealed the methylene signals (multiplet) at δ 1.86 and δ 2.00 which were characteristic of the 6-deoxy moiety from 6d-ido-Hep and a broad range of overlapping sugar ring proton resonances between δ 3.30 and δ 4.55. 1D $^{31}$P NMR detected two resonances at δp 14.1 and δp 14.4 which were typical of MeOPN signals (FIG. 15B).

It was determined that *C. jejuni* strain MK16 (serotype HS:13) CPS consists of the following disaccharide repeats in quasi equal concentrations (with MeOPN non-stoichiometrically attached to C-2 and C-7 of 6d-β-ido-Hep):
- [→3)-6d-β-D-ido-Hep-(1→4)-β-Glc-(1→]; and
- [→3)-L-β-D-ido-Hep-(1→4)-β-Glc-(1→].

*C. jejuni* Serotype HS3/13/50

HS: 3:13:50 complex has been identified predicated on a quantitatively low level immune-cross reactivity. *C. jejuni* strain BH-01-0142 (serotype HS: 3:13:50) was composed of galactose (Gal), 6-deoxy-ido-heptose (6d-ido-Hep), and L-glycero-D-ido-heptose (LD-ido-Hep) using GS-MS using alditol acetate derivative profile determination for compositional analysis of *C. jejuni* BH-01-0142 CPS (serotype HS:3:13:50)). The sugar linkage types: 4-substituted galactose [→4)-Gal-(1→], 3-substituted 6-deoxy-heptose [→3)-6d-Hep-(1-4] and 3-substituted L-glycero-D-ido-heptose [→3)-LD-ido-Hep-(1→] were found to make up the CPS of serotype HS:3:13:50, using GC-MS profile analysis of permethylated alditol acetate derivatives of *C. jejuni* BH-01-0142 CPS (serotype (HS: 3:13:50)). In addition, minor components, 3,4-di-substituted galactose [→3,4)-Gal-(1→], 2,3-di-substituted 6-deoxy-heptose [→2,3)-6d-Hep-(1→], and 2,3-di-substituted L-glycero-D-ido-heptose [→2,3)-LD-ido-Hep-(1→] were also characterized. The above results suggested that the backbone units of *C. jejuni* serotype HS: 3,13,50 CPS were [→4)-Gal-(1→], [→3)-6d-Hep-(1→], and [→3)-LD-ido-Hep-(1→], with three other non-sugar components were non-stoichiometrically attached to the C-3 of Gal, and C-2 of 6d-ido-Hep and LD-ido-Hep. Also, a terminal Gal [Gal-(1→] was also determined and was suggested as a non-reducing end.

The $^1$H NMR spectrum of the *C. jejuni* serotype HS:3: 13:50 CPS showed broad overlapping peaks between δ 5.00 ppm and δ 5.30 ppm representing the anomeric proton signals. These overlapping peaks suggested the presence of α-anomeric sugars. In addition, the $^1$H NMR spectrum also revealed a methylene signal at δ 1.80 and δ 2.02 which are characteristic of 6-deoxy moiety from 6d-ido-Hep. Another proton resonance at δ 2.72 was later confirmed as a methylene signal which also revealed in the $^1$H NMR spectrum.

In order to obtain the information for the non-sugar component, $^{31}$P NMR of the *C. jejuni* BH-01-0142 CPS was performed to determine any phosphorus substituents. The phosphorus resonances at δp 15.3 revealed the presence of an O-methyl phosphoramidate groups (MeOPN) or CH$_3$OP (O)NH$_2$(OR), which was involved in the structural moiety in the serotype HS:3,13,50 of *C. jejuni* CPS. The appearance of one MeOPN signal suggested this unique component was partially attached to one of the monosaccharide residues in the CPS of *C. jejuni* strain BH-01-0142, since the results of sugar linkage type analysis revealed the presence of minor component of 1,3,4-linked Gal, 1,2,3-linked 6d-ido-Hep and 1,2,3-linked LD-ido-Hep.

Figure 16:
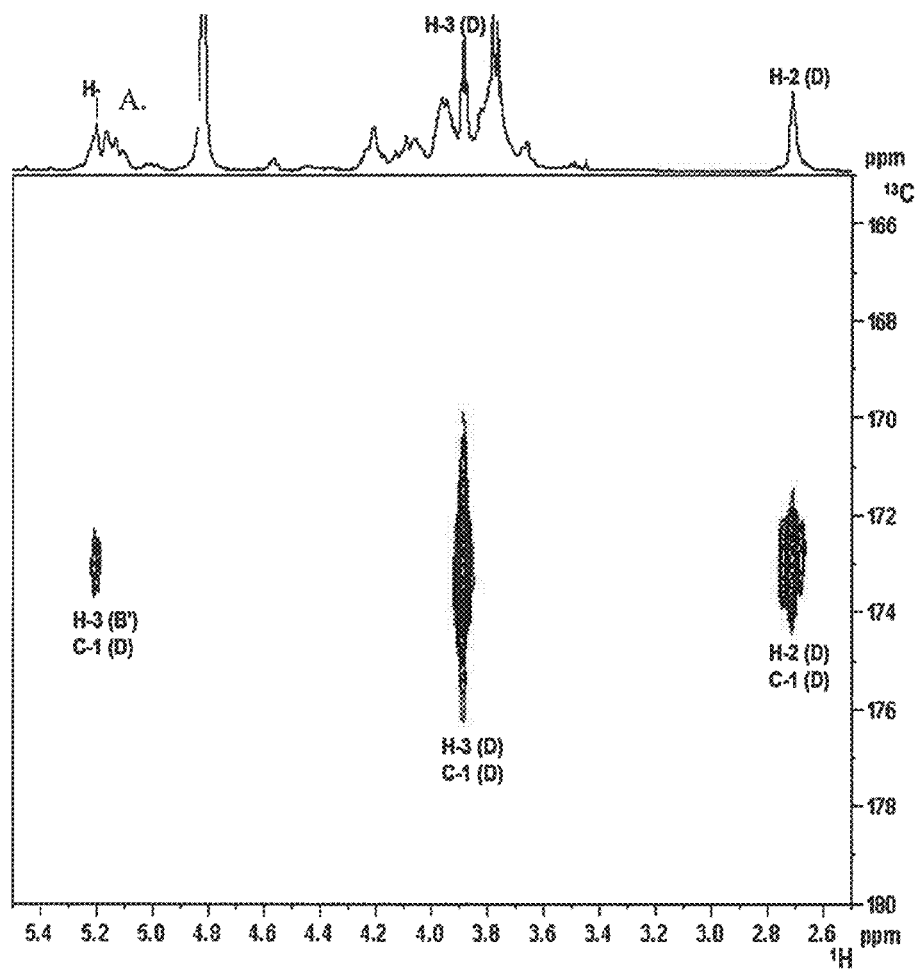
FIG. 16. Linkage determination of MeOPN group by NMR. 2D $^1$H-$^{31}$P HMBC NMR spectrum of *C. jejuni* BH-01-0142 CPS (A': 1,2,3-linked 6d-ido-Hep/LD-ido-Hep with C residue; C: MeOPN).
Figure 16:
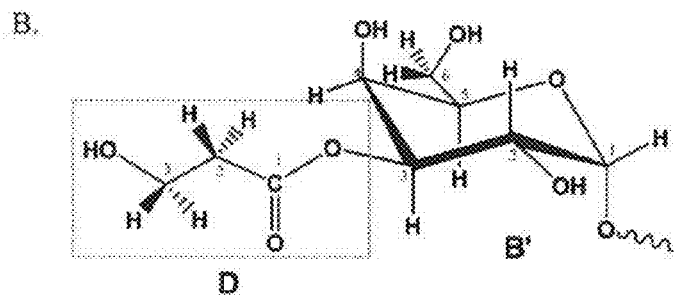

2D $^1$H-$^{31}$P HMBC NMR of *C. jejuni* BH-01-0142 CPS was carried out to elucidate the linkage site of the MeOPN group (FIG. 16). The cross-peak at δp 15.3/δ$_H$ 3.78 represented the correlation between the phosphorus and the methyl group of the MeOPN. A strong proton-phosphorus correlation between δp 15.3 and δ$_H$ 4.56 suggested the linkage site of the MeOPN group, with also a weak proton-phosphorus correlation between δp 15.3 and the anomeric proton at $\delta_H$ 5.10. Thus, the combination of the results from monosaccharide linkage type analysis and 2D $^1$H-$^{31}$P HMBC NMR showed that the O-methyl-phosphoramidate group (residue C) was attached to the C-2 position of 6d-ido-Hep and LD-ido-Hep (residue A').

Figure 17:
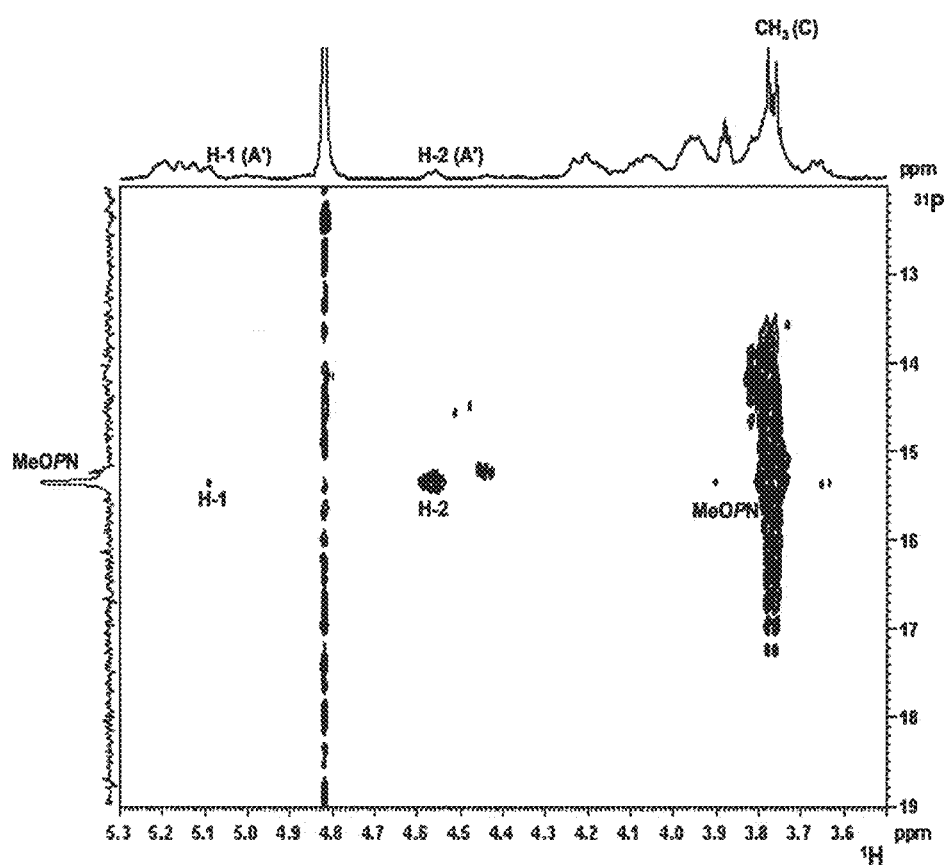
FIG. 17. NMR analysis showing that non-sugar moiety was 3-hydroxypropanoyl. (A) 2D $^1$H-$^{13}$C HMBC NMR spectrum of *C. jejuni* BH-01-0142 CPS (B': 1,3,4-linked Gal with residue D; (B) D: 3-hydroxypropanoyl group.

A 2D $^1$H-$^{13}$C HMBC NMR experiment (FIG. 17) showed that a second non-sugar moiety was that of 3-hydroxypropanoyl. The cross-peaks at $\delta_H$ 3.89/$\delta_C$ 173.0 and $\delta_H$ 2.72/$\delta_C$ 173.0 showed three-bond and two-bond connectivities of the carbonyl ester C-1 with H-3 and H-2 of 3-hydroxypropanoyl group (residue D), respectively. The 3-hydroxypropanoyl group was observed to be connected to the C-3 of Gal, by interpreting the cross-peak at $\delta_H$ 5.20/$\delta_C$ 173.0, and also by taking into account the results from linkage type analysis that showed a minor peak of 1,3,4-linked Gal.

We determined that *C. jejuni* serotype HS:3 has a CPS with the disaccharide repeat (with non-stoichiometric substitutions of O-methyl phosphoramidate at C-2 of 6d-α-ido-Hep/L-α-D-ido-Hep and 3-hydroxypropanoyl ester at C-3 of α-Gal):

[→3)L-α-D-ido-Hep-(1→4)-α-Gal-(1→]; and
[→3)-6d-α-ido-Hep-(1→4)-α-Gal-(1→].

Example 5: Immunogenic Composition

An immunogenic composition against *C. jejuni* is can comprise one or more isolated *C. jejuni* polysaccharides or polysaccharide polymers. The composition contains the polysaccharides or polysaccharide polymers free of LOS, which is associated with Guillain-Barré Syndrome. An embodiment is a composition comprising one or more isolated *C. jejuni* derived polysaccharides or polysaccharide polymers, with the polysaccharide polymer comprising 1 to 100 polysaccharides linked together (i.e., "n" greater than or equal to 1). The structures of the isolated *C. jejuni* polysaccharide are derived from one or more of the strains HS5, HS1, HS2, HS3, HS4, HS4/13/64, HS50 and HS13.

In one embodiment, the composition comprises one or more polysaccharide structures selected from the group consisting of:

```
[MeOPN]~——
      |
      ↓
      7
   α-Dideoxy-Hep
      1
      |
      ↓
      6
→7)α-DD-Hep(1→3)Glucitol(6→P→
   2            2
   ↑            ↑
   |            |
   1            1
α-Dideoxy-Hep  α-Dideoxy-Hep
   7            7
   ↑            ↑
   |            |
[MeOPN]~——  [MeOPN]~——;
```

```
[MeOPN]~——
      |
      ↓
      7
   α-Dideoxy-Hep
      1
      |
      ↓
      6
→7)α-DD-Hep(1→2)Glucitol(6→P→
      2
      ↑
      |
      1
   α-Dideoxy-Hep
      7
      ↑
      |
   [MeOPN]~——;
→7)α-DD-Hep(1→2)Glucitol(6→P→
      2
      ↑
      |
      1
   α-Dideoxy-Hep
      7
      ↑
      |
   [MeOPN]~——;
→7)α-DD-Hep(1→3)Glucitol(6→P→
   2            2
   ↑            ↑
   |            |
   1            1
α-Dideoxy-Hep  α-Dideoxy-Hep
   7            7
   ↑            ↑
   |            |
[MeOPN]~——  [MeOPN]~——;
```

[→4)-α-D-Galp-(1→2)-Gro-(1→P→]$_n$, derived from *C. jejuni* strain HS44; and

```
[→4)-α-D-Galp-(1→2)-Gro-(1→P→]n,
         3      2
         ↑      ↑
         1      1
[MeOPN]→3)-Fruf  Fruf-(3←[MeOPN]
``` from *C. jejuni* strain HS1 and/or HS1/44;

[→3)-L-β-D-ido-Hep-(1→4)-β-D-GlcNAc-(1→]$_n$, derived from *C. jejuni* strain HS4/HS13/HS64, with non-stoichiometric substitution of O-methyl-phosphoramidate at position 2 of L-D-ido-heptose;

[→3)-6d-β-D-ido-Hep-(1→4)-β-D-GlcNAc-(1→]$_n$, derived from *C. jejuni* strain HS4/13/64, with non-stoichiometric MeOPN at C-2 and/or C-7 of 6d-ido-Hep;

[→3)-L-β-D-ido-Hep-(1→4)-β-D-GlcNAc-(1→]$_n$, derived from *C. jejuni* strain HS4, with non-stoichiometric MeOPN at C-4 of LD-ido-Hep;

[→3-6d-β-D-ido-Hep-(1→4)-β-D-Glc-(1→]$_n$, derived from *C. jejuni* strain HS13, without MeOPN or with non-stoichiometric MeOPN at C-2 and/or C-7 of 6d-ido-Hep;

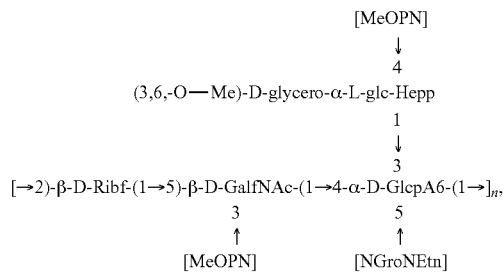

NGro=aminoglycerol; Etn=ethanolamine, derived from HS2;

[→3)-L-alpha-D-ido-Hep-(1→4)-alpha-Gal-(1→]$_n$, derived from *C. jejuni* strain HS3, with non-stoichiometric substitution O-methyl-phosphoramidate at position 2 of 6-deoxy-alpha-D-ido-heptose with or without a 3-hydroxypropanoyl ester at C-3 of α-Gal;

[→3)-L-β-D-ido-Hep-(1→4)-β-D-Glc-(1→]$_n$, derived from HS50, with non-stoichiometric MeOPN at C-4 of LD-ido-Hep; and

[→3-6d-β-D-ido-Hep-(1→4)-β-D-Glc-(1→]$_n$, derived from *C. jejuni* strain HS50, with non-stoichiometric MeOPN at C-7 of 6d-ido-Hep, wherein the same polysaccharide is linked to form a polysaccharide polymer comprising 1 to 100 polysaccharides linked together (i.e., "n" greater than or equal to 1).

The polysaccharides or polysaccharide polymers of the decomposition can be linked to a carrier, wherein said carrier can be a protein. In one embodiment, the protein carrier is CRM$_{197}$.

Example 6: Induction of Immune Response by CPS Conjugates

Induction of Immune Response Against HS1, HS1/HS44 and HS44

In one embodiment an immunogenic composition, useful for inclusion in a vaccine composition against HS1, HS1/HS44 and HS44 *C. jejuni* strains, comprises a polysaccharide, comprising the structure:

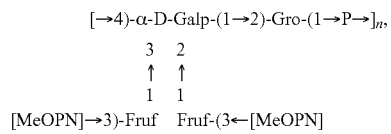

or a polymer comprising a repeating of the polysaccharide structure, where "n". In an alternative embodiment, the immunogenic composition can comprise the HS44 composition, as in Example 1, which does not contain the "[MeOPN]→3)-Fruf" unit.

Figure 18:
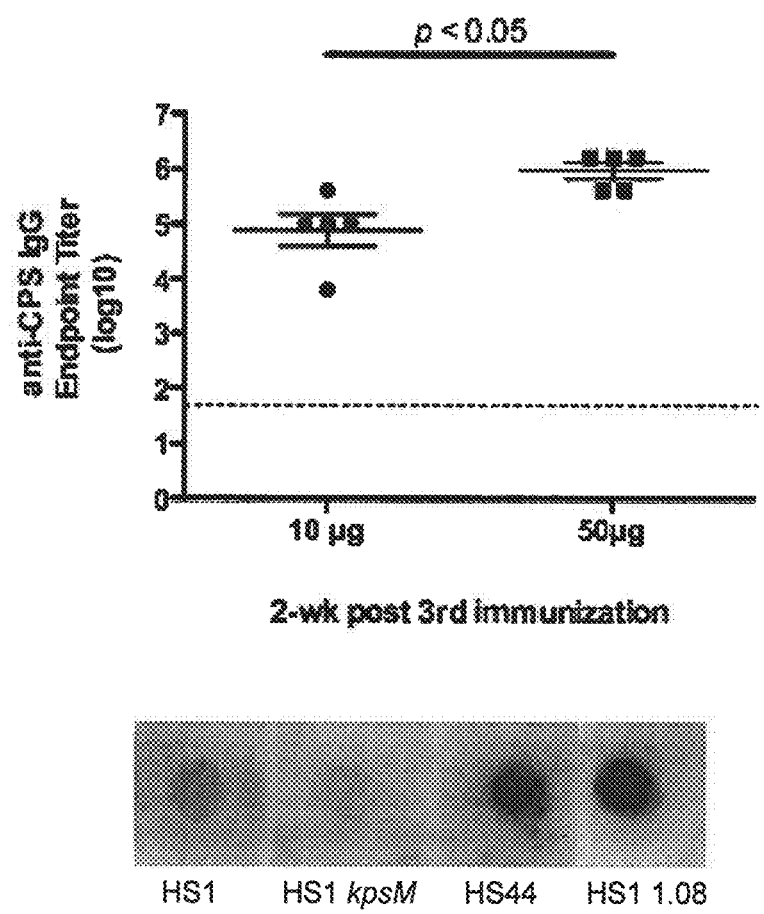
FIG. 18. Immunogenicity of HS1-CRM$_{197}$ conjugate in mice. A. ELISA titers to HS1-BSA two weeks after three doses. B. Dot blot of *C. jejuni* cells immunodetected with mouse sera at a final dilution of 1:1000.

Surprisingly, the above structure found in HS1 and HS1/HS44 strains induces an immune response against HS44 strains. In the study, mice were immunized with escalating amounts of vaccine administered with Alhydrogel® (Clifton, N.J.). Two weeks following the final immunization, all immunized animals exhibited significant levels of serum IgG antibodies specific against HS1 CPS (P<0.05) compared to pre-immune sera. Furthermore, this effect was dose dependent as mice immunized with 50 µg of vaccine (by weight) per dose had a significantly higher endpoint titer (P<0.05) than mice receiving 10 µg per dose. These results illustrate that HS1 is capable of generating high levels of anti-CPS antibodies in mice. The results of these studies is illustrated in FIG. 18. Also, shown in FIG. 19, a dot blot demonstrating immunogenicity of an HS1-CRM197 vaccine. Purified capsules (1 mg/ml) were dot blotted in triplicate (2 µl each) to nitrocellulose and immunodetected with rabbit polyclonal antiserum to an HS1-CRM197 vaccine. HS1, wildtype HS1 capsule; HS1.08, capsule from a fructose transferase mutant of HS1 that lacks the fructose branch and the MeOPN; HS23/36, capsule from 81-176 which expresses a heterologous capsule (HS23/36).

Induction of an Immune Response Using an HS-5 Polysaccharide Composition

The ability of isolated HS5 polysaccharide to induce an immune response was evaluated. It is contemplated that isolated HS5 polysaccharide could be used conjugated to any of a number of protein carriers. However, as an illustration, CRM$_{197}$-conjugated HS5 polysaccharide was evaluated.

Figure 19:
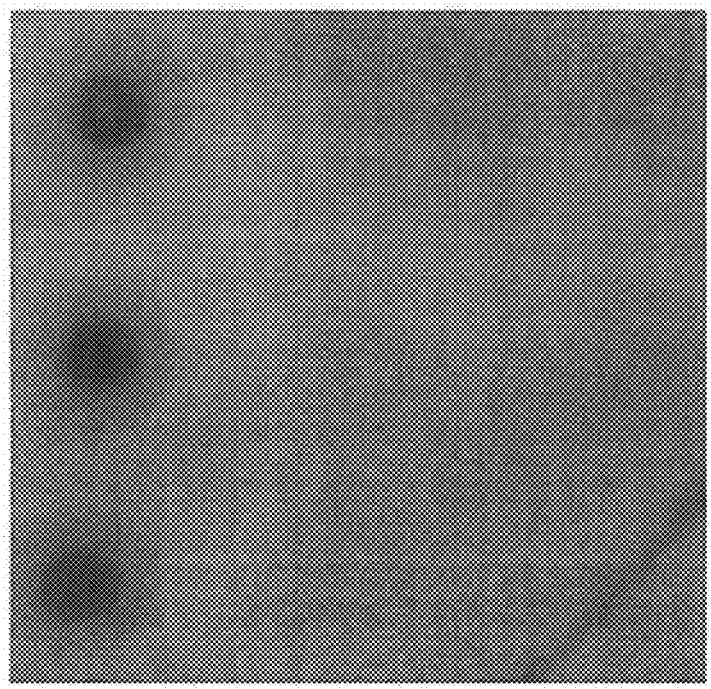
FIG. 19. Immune response to HS5-CRM$_{197}$ conjugate. Mice were immunized with three (3) doses (10 μg and 50 μg by weight of conjugate) given at 4 week intervals. The mice were bled two weeks after the last doses.

In this study, HS5 was conjugated to CRM$_{197}$ predicated on the method in Example 3. BALB/c mice were given three doses each of 10 µg or 50 µg of HS5 polysaccharide-conjugate at 4 week intervals, with 200 µg of ALHYDROGEL® (Brenntag AG, Germany). The mice received a total of three injections. Two weeks after the last dose, the mice were bled and the sera evaluated by ELISA. The results of this study are shown in FIG. 19 showing CPS-specific IgG responses.

Figure 20:
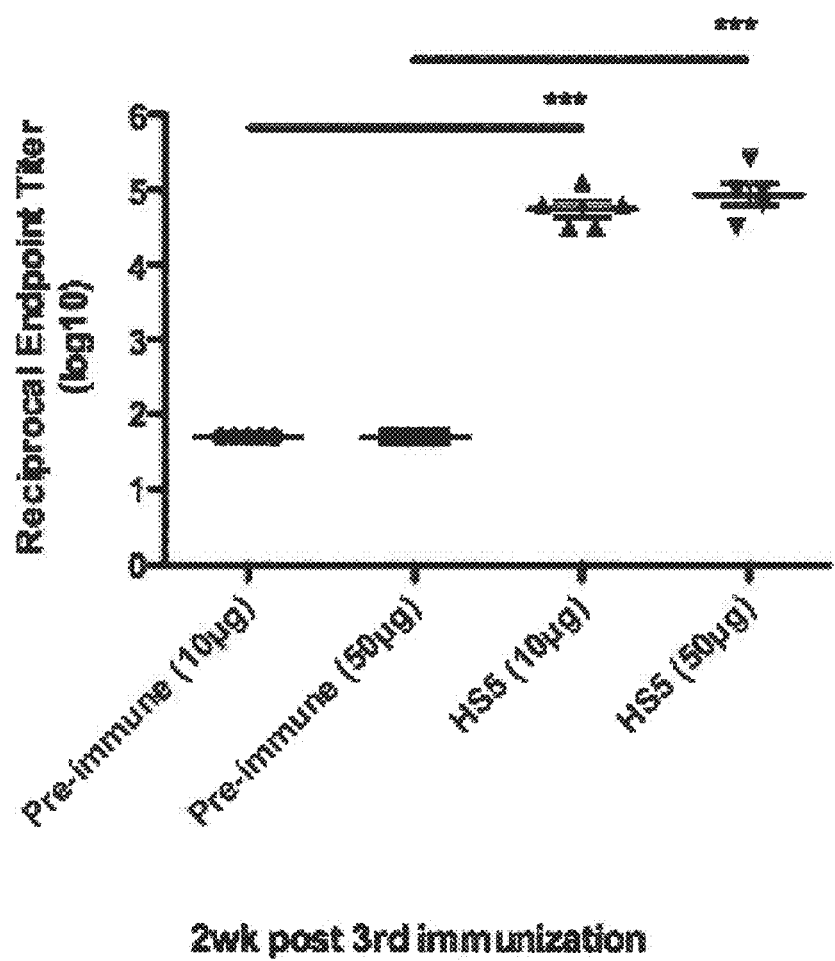
FIG. 20. BH0142 (HS3) conjugate vaccine is immunogenic in mice. Data represent the mean (±SEM) reciprocal IgG endpoint titer per treatment group.
Figure 21:
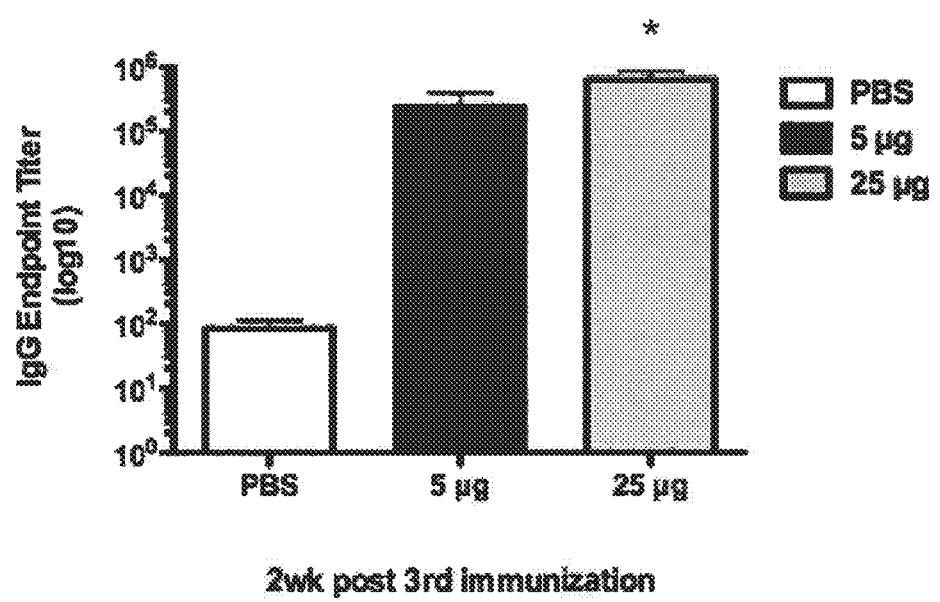
FIG. 21. Dot blot demonstrating immunogenicity of an HS1-CRM197 vaccine. Purified capsules (1 mg/ml) were dot blotted in triplicate (2 μl each) to nitrocellulose and immunodetected with rabbit polyclonal antiserum to an HS1-CRM197 vaccine. HS1, wildtype HS1 capsule; HS1.08, capsule from a fructose transferase mutant of HS1 that lacks the fructose branch and the MeOPN; HS23/36, capsule from 81-176 which expresses a heterologous capsule (HS23/36).

The immune response of HS3 conjugated to CRM$_{197}$ was also examined. Female BALB/c mice were immunized via subcutaneous injection with conjugate vaccine (HS3 from BH0142 conjugated to CRM$_{197}$) in aluminum hydroxide 3 times at 4-week intervals. Vaccine was given by weight. A dose of 5 µg corresponded to approximately 0.5 µg of conjugated polysaccharide and a dose of 25 µs corresponded to approximately 2.5 µg of conjugated polysaccharide. Serum was collected 2-weeks following each immunization. Capsule-specific IgG responses were determined by ELISA. The results are shown in FIG. 20.

Additionally, the immune cross-reactions among members of the HS4 complex were evaluated. In these studies, whole cell proteinase K digested samples of various members of the HS4 complex were electrophoresed on 12.5% SDS-PAGE gels and immunoblotted with rabbit polyclonal antisera made against formalin killed whole cells of members of the HS4 complex. HS4 anti-serum was found to cross react to HS13 and HS4. Anti-HS4/13/64 serum was found to cross-react with HS64 and HS4 and to a small extent to HS50.

In similar studies, rabbit anti-HS13 serum was found to cross react with HS4 and HS13 and anti-HS64 serum was found to cross react with HS4, HS13, HS4/13/64 and HS50. Similarly, rabbit polyclonal antiserum made to conjugate vaccine composed of the capsule of HS4/13/64 strain conjugated to CRM$_{197}$ was used in an immunoblot to determine the cross reactivity of the vaccine to proteinase K digested whole cell preparations of other members of the HS4 complex. Antibodies to the vaccine cross-reacted to HS4 and HS64, but not to HS13 or HS50.

Example 7: Method for Inducing an Anti-*C. jejuni* Immune Response in Mammals

An embodiment of the invention is the induction of an immune response against capsule polysaccharide. The embodied method comprising administering an immunogenic composition comprising one or more polysaccharide antigens, wherein each polysaccharide antigen comprises a *C. jejuni* capsule polysaccharide polymer. The *Campylobacter jejuni* capsule polysaccharide polymers comprise of *C. jejuni* strains, as in Examples 1-4. As such, a capsule polysaccharide polymer comprises 1 to 100 copies of a polysaccharide structure, derived from an individual *C. jejuni* strain, connected together to form a polysaccharide polymer. Induction of immunity can be against one or more strains of *C. jejuni*.

The capsule polysaccharide are derived from one or more *C. jejuni* strains selected from the group consisting of HS1 and HS1 complex (HS1, HS1/HS44 or HS44), HS2, HS3, HS4, HS5, HS13, HS4/13/64, and HS50. The inventive immunogenic compositions would comprise isolated *C. jejuni* polysaccharide structures or polysaccharide polymers of the structures, without lipooligosaccharide, or other structures associated with GBS. The polysaccharide polymers can be conjugated or unconjugated to a carrier molecule and the composition administered at a dose range of 0.1 µg to 10 mg per dose with or without an adjuvant.

Another embodiment is a method of to induce an immune response against *C. jejuni* by administering isolated *C. jejuni* capsule polysaccharide derived from HS1, HS1/HS44 or HS44. In the inventive method, the composition is used to induce an immune response against HS1, HS1/HS44 or HS44. As an example, a composition comprising isolated *C. jejuni* capsule polysaccharide, isolated away from or purified from LOS components and other components that can cause autoimmune responses such as Guillain-Barre syndrome, such as derived from HS1, are used to induce an immune response against HS1, HS1/HS44 and HS44 *C. jejuni* strains.

In another embodiment, a composition comprising one or more of the polysaccharide comprising one or more of polysaccharides derived from HS4, HS13, HS4/HS13/HS64 or HS50 can be used in a method to induce immunity against any of the *C. jejuni* strains of the HS4 complex, comprising HS4, HS13, HS4/HS13/H64 or HS50.

In the above described compositions, the polysaccharides or polysaccharide polymers can be linked to a carrier, wherein said carrier can be a protein. In one embodiment, the protein carrier is $CRM_{197}$.

As an example, the embodiment method, comprises the steps:

a. administering an immunogenic composition comprising one or more *C. jejuni* isolated capsule polysaccharide polymers derived from capsules of *C. jejuni* strains selected from the group consisting of: HS1 and HS1 complex (HS1, HS1/HS44 or HS44), HS2, HS3, HS4, HS5, HS13, HS4/13/64, and HS50, wherein capsule polysaccharides of a strain can be linked to form a polysaccharide polymer comprises 1 to 100 copies of a polysaccharide structure, derived from an individual *C. jejuni* strain, connected together to form a polymer and wherein said composition would comprise isolated *C. jejuni* polysaccharide structures or polymers of the structures, without lipooligosaccharide, or other structures associated with GBS and wherein the polysaccharide or polysaccharide polymers can be conjugated or unconjugated to a carrier molecule and the composition administered at a dose range of 0.1 µg to 10 mg per dose with or without an adjuvant, and wherein the polysaccharide structures include one or more of the following structures selected from the group consisting of:

```
[MeOPN]~ ──
    │
    ▼
    7
α-Dideoxy-Hep
    1
    │
    ▼
    6
→7)α-DD-Hep(1→3)Glucitol(6→P→
    2           2
    ▲           ▲
    │           │
    1           1
α-Dideoxy-Hep  α-Dideoxy-Hep
    7           7
    ▲           ▲
    │           │
[MeOPN]~ ──  [MeOPN]~ ── ;
```

```
[MeOPN]~ ──
    │
    ▼
    7
α-Dideoxy-Hep
    1
    │
    ▼
    6
→7)α-DD-Hep(1→2)Glucitol(6→P→
    2
    ▲
    │
    1
α-Dideoxy-Hep
    7
    ▲
    │
[MeOPN]~ ── ;
```

-continued

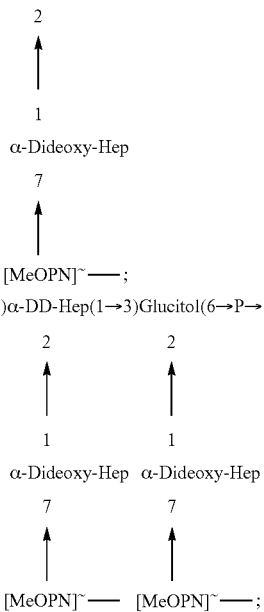

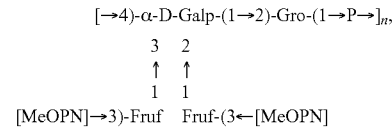

[→4)-α-D-Galp-(1→2)-Gro-(1→P→]$_n$, derived from the derived from the *C. jejuni* strain HS44;

from the *C. jejuni* strain HS1 and/or HS1/44;
[→3)-L-β-D-ido-Hep-(1→4)-β-D-GlcNAc-(1→]$_n$,
    derived from HS4/HS13/HS64,
with non-stoichiometric substitution of O-methyl-phosphoramidate at position 2 of L-D-ido-heptose;
[→3)-6d-β-D-ido-Hep-(1→4)-β-D-GlcNAc-(1→]$_n$,
    derived from HS4/13/64, with non-stoichiometric MeOPN at C-2 and/or C-7 of 6d-ido-Hep;
[→3)-L-β-D-ido-Hep-(1→4)-β-D-GlcNAc-(1→]$_n$,
    derived from HS4, with non-stoichiometric MeOPN at C-4 of LD-ido-Hep;
[→3-6d-β-D-ido-Hep-(1→4)-β-D-Glc-(1→]$_n$, derived from HS13, without MeOPN or with non-stoichiometric MeOPN at C-2 and/or C-7 of 6d-ido-Hep;

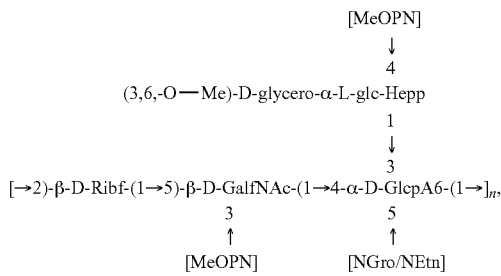

derived from HS2, wherein NGro=aminoglycerol; Etn=ethanolamine;

[→3)-L-alpha-D-ido-Hep-(1→4)-alpha-Gal-(1→]$_n$,
    derived from HS3, with non-stoichiometric substitution O-methyl-phosphoramidate at position 2 of 6-deoxy-alpha-D-ido-heptose with or without a 3-hydroxypropanoyl ester at C-3 of α-Gal;
[→3)-L-β-D-ido-Hep-(1→4)-β-D-Glc-(1→]$_n$, derived from HS50, with non-stoichiometric MeOPN at C-4 of LD-ido-Hep;
and
[→3-6d-β-D-ido-Hep-(1→4)-β-D-Glc-(1→]$_n$, derived from HS50, with non-stoichiometric MeOPN at C-7 of 6d-ido-Hep,
wherein the same polysaccharide is linked to form a polysaccharide polymer comprising 1 to 100 polysaccharides linked together (i.e., "n" greater than or equal to 1);
b. administering a boosting dose of the composition as described in step (a), with or without adjuvant at a dose range of 0.1 µg to 10 mg per dose.

Another embodiment comprises a method of immunizing against *Campylobacter jejuni* strains HS1; HS1/HS44 and/or HS44 by the administration of a composition comprising one or more isolated *C. jejuni* capsule polysaccharides. The method comprises the steps:
a. administering an immunogenic composition comprising one or more *C. jejuni* capsule polysaccharide polymers. The *C. jejuni* capsule polysaccharide polymers comprise polysaccharide structures derived from capsules of *C. jejuni* strains selected from the group consisting of HS1, HS1/HS44, HS44, wherein a capsule polysaccharide polymer comprises 1 to 100 copies of a polysaccharide structure, derived from an individual *C. jejuni* strain, connected together to form a polymer, without lipooligosaccharide, or other structures associated with GBS administered at a dose range of 0.1 µg to 10 mg per dose with or without an adjuvant. The polysaccharide structures include one or more of the following structures selected from the structures:
[→4)-α-D-Galp-(1→2)-Gro-(1→P→]$_n$, derived from the derived from the *C. jejuni* strain HS44; or

from the *C. jejuni* strain HS1 and/or HS1/44;
wherein the same polysaccharide is linked to form a polysaccharide polymer comprising 1 to 100 polysaccharides linked together (i.e., "n" greater than or equal to 1);
b. administering a boosting dose of the composition as described in step (a), with or without adjuvant at a dose range of 0.1 µg to 10 mg per dose.

Another embodiment comprises a method of immunizing against *Campylobacter jejuni* strains HS4, HS13, HS4/HS13/H64 or HS50 by the administration of a composition comprising one or more isolated *C. jejuni* capsule polysaccharides derived from HS4, HS13, HS4/HS13/H64 or HS50. The method comprises the steps:
a. administering an immunogenic composition comprising one or more *C. jejuni* capsule polysaccharides derived from HS4, HS13, HS4/HS13/H64 or HS50, wherein a capsule polysaccharide polymer comprising 1 to 100 copies of a polysaccharide structure, connected together to form a polymer, without lipooligosaccharide, or other structures associated with GBS, administered at a dose range of 0.1 µg to 10 mg per dose with or without an adjuvant and wherein the polysaccharide structures include one or more of the following structures selected from the structures:

[→3)-L-β-D-ido-Hep-(1→4)-β-D-GlcNAc-(1→]$_n$, derived from HS4/HS13/HS64, with non-stoichiometric substitution of O-methyl-phosphoramidate at position 2 of L-D-ido-heptose;

[→3)-6d-β-D-ido-Hep-(1→4)-β-D-GlcNAc-(1→]$_n$, derived from HS4/13/64, with non-stoichiometric MeOPN at C-2 and/or C-7 of 6d-ido-Hep;

[→3)-L-β-D-ido-Hep-(1→4)-β-D-GlcNAc-(1→]$_n$, derived from HS4, with non-stoichiometric MeOPN at C-4 of LD-ido-Hep;

[→3-6d-β-D-ido-Hep-(1→4)-β-D-Glc-(1→]$_n$, derived from HS13, without MeOPN or with non-stoichiometric MeOPN at C-2 and/or C-7 of 6d-ido-Hep;

[→3)-L-β-D-ido-Hep-(1→4)-β-D-Glc-(1→]$_n$, derived from HS50, with non-stoichiometric MeOPN at C-4 of LD-ido-Hep; and [→3-6d-β-D-ido-Hep-(1→4)-β-D-Glc-(1→]$_n$, derived from HS50, with non-stoichiometric MeOPN at C-7 of 6d-ido-Hep, wherein the same polysaccharide is linked to form a polysaccharide polymer comprising 1 to 100 polysaccharides linked together (i.e., "n" greater than or equal to 1);

b. administering a boosting dose of the composition as described in step (a), with or without adjuvant at a dose range of 0.1 µg to 10 mg per dose.

The polysaccharide polymers can be conjugated or unconjugated to a carrier molecule and the composition. In the above method, immunogenic composition can be administered orally, nasally, subcutaneously, intradermally, transdermally, transcutaneously, intramuscularly or rectally. Also, the carrier molecule can be a protein, for example $CRM_{197}$, or a non-protein molecule. Adjuvants can be any of a number of adjuvants. Examples of adjuvants include: LTR 192G, Aluminum hydroxide, RC529, QS21, E294, oligodeoxynucleotides (ODN), CpG-containing oligodeoxynucleotides, and aluminum phosphate.

Obviously, many modifications and variations of the present invention are possible, in light of the above teachings. It is therefore to be understood that, within the scope of the appended claims, the invention may be practiced otherwise than as specifically described.

What is claimed is:

1. An immunogenic composition against *Campylobacter jejuni* comprising one or more polysaccharide antigens, wherein each of said polysaccharide antigens comprises an isolated *Campylobacter jejuni* capsule polysaccharide derived from a *Campylobacter jejuni* strain to form a repeating polysaccharide polymer comprising 2 or more of said capsule polysaccharide, wherein said *Campylobacter jejuni* strains are selected from the group consisting of HS4, HS4/13/64, HS5, and HS50, wherein said immunogenic composition does not contain *Campylobacter jejuni* lipooligosaccharide structures associated with Guillain Barré Syndrome, wherein said polysaccharide polymer is conjugated to a protein carrier, wherein the structure of HS4 is →3)-L-β-D-ido-Hep-(1→4)-β-D-GlcNAc-(1→, with non-stoichiometric MeOPN at C-4 of LD-ido-Hep, wherein the structure of HS4/13/64 is [→3)-6d-β-D-ido-Hep-(1→4)-β-D-GlcNAc-(1→]$_n$, with non-stoichiometric MeOPN at C-2 and/or C-7 of 6d-ido-Hep, and wherein the number of repeats of a capsule polysaccharide "n" is 1 to 100.

2. The immunogenic composition of claim 1, wherein said isolated *Campylobacter jejuni* capsule polysaccharide comprises a polysaccharide structure selected from the group consisting of:

```
[MeOPN]˜—
   │
   ↓
   7
α-Dideoxy-Hep
   1
   │
   ↓
   6
→7)α-DD-Hep(1→3)Glucitol(6→P→
   2           2
   ↑           ↑
   │           │
   1           1
α-Dideoxy-Hep  α-Dideoxy-Hep
   7           7
   ↑           ↑
   │           │
[MeOPN]˜—   [MeOPN]˜—;

[MeOPN]˜—
   │
   ↓
   7
α-Dideoxy-Hep
   1
   │
   ↓
   6
→7)α-DD-Hep(1→2)Glucitol(6→P→
   2
   ↑
   │
   1
α-Dideoxy-Hep
   7
   ↑
   │
[MeOPN]˜—;

→7)α-DD-Hep(1→2)Glucitol(6→P→
   2
   ↑
   │
   1
α-Dideoxy-Hep
   7
   ↑
   │
[MeOPN]˜—;
```

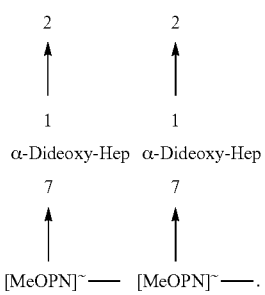

derived from HS5;

[→3)-L-β-D-ido-Hep-(1→4)-β-D-Glc-(1→]$_n$, derived from HS50, with non-stoichiometric MeOPN at C-4 of LD-ido-Hep; and

[→3-6d-β-D-ido-Hep-(1→4)-β-D-Glc-(1→]$_n$, derived from HS50, with non-stoichiometric MeOPN at C-7 of 6d-ido-Hep;

wherein the number of repeats of a capsule polysaccharide "n" is 1 to 100.

3. The immunogenic composition of claim 1 or claim 2, wherein said protein carrier is $CRM_{197}$.

4. The immunogenic composition of claim 1 or claim 2, wherein said composition also comprises an adjuvant.

5. The immunogenic composition of claim 4, wherein said adjuvant is selected from the group consisting of LTR192G, aluminum hydroxide, RC529, QS21, E294, oligodeoxynucleotides (ODN), CpG-containing oligodeoxynucleotides, and aluminum phosphate.

6. A method of inducing an anti-*Campylobacter jejuni* immune response in a mammal against a *Campylobacter jejuni* strain selected from the group consisting of HS4, HS4/13/64, HS5, and HS50, comprising:

a. administering the immunogenic composition of claim 1 or claim 2 to said mammal at a dose range of 0.1 μg to 10 mg per dose; and b. administering a boosting dose of said immunogenic composition of claim 1 or claim 2 to said mammal at a dose range of 0.1 μg to 10 mg per dose.

7. The method of claim 6, wherein said protein carrier is $CRM_{197}$.

8. The method of claim 6, wherein said immunogenic composition also comprises an adjuvant.

9. The method of claim 8, wherein said adjuvant is selected from the group consisting of LTR192G, aluminum hydroxide, RC529, QS21, E294, oligodeoxynucleotides (ODN), CpG-containing oligodeoxynucleotides, and aluminum phosphate.

10. The method of claim 6, wherein said immunogenic composition is administered by a route selected from the group consisting of: orally, nasally, subcutaneously, intradermally, transdermally, transcutaneously, intramuscularly and rectally.

11. A method of inducing an anti-*Campylobacter jejuni* immune response in a mammal against a *Campylobacter jejuni* strain selected from the group consisting of HS4, HS4/13/64, HS5, and HS50, comprising administering 3 doses of the immunogenic composition of claim 1 or claim 2 to said mammal, at a dose range of 0.1 μg to 10 mg per dose, with or without an adjuvant.

12. The method of claim 11, wherein said adjuvant is selected from the group consisting of LTR192G, aluminum hydroxide, RC529, QS21, E294, oligodeoxynucleotides (ODN), CpG-containing oligodeoxynucleotides, and aluminum phosphate.

13. The method of claim 11, wherein said immunogenic composition is administered by a route selected from the group consisting of: orally, nasally, subcutaneously, intradermally, transdermally, transcutaneously, intramuscularly and rectally.

* * * * *